United States Patent [19]

Farmer

[11] Patent Number: 5,425,858
[45] Date of Patent: Jun. 20, 1995

[54] METHOD AND APPARATUS FOR CAPACITIVE DEIONIZATION, ELECTROCHEMICAL PURIFICATION, AND REGENERATION OF ELECTRODES

[75] Inventor: Joseph Farmer, Tracy, Calif.

[73] Assignee: The Regents of the University of California, Oakland, Calif.

[21] Appl. No.: 246,692

[22] Filed: May 20, 1994

[51] Int. Cl.[6] .............................................. C02F 1/461
[52] U.S. Cl. ..................................... 204/149; 204/164; 204/186; 204/267; 204/272; 204/302; 210/748
[58] Field of Search ............... 204/149, 186, 267, 272, 204/164, 302; 210/748

[56] References Cited

U.S. PATENT DOCUMENTS

| | | | |
|---|---|---|---|
| 3,859,195 | 1/1975 | Williams | 204/272 |
| 3,883,412 | 5/1975 | Jensen | 204/149 |
| 5,260,855 | 11/1993 | Kaschmitter et al. | 361/502 |

OTHER PUBLICATIONS

Allan M. Johnson et al., "The Electrosorb Process for Desalting Water", Mar. 1970, The Office of Saline Water Research and Development Progress Report No. 516, U.S. Department of the Interior PB 200 056.

A. M. Johnson and John Newman, "Desalting by Means of Porous Carbon Electrodes", Mar. 1971, pp. 510–517, J. Electrochem. Soc.: Electrochemical Technology (vol. 118, No. 3).

Gary C. Ganzi, Jonathan H. Wood, Christopher S. Griffin, "Water Purification and Recycling Using the CDI Process", Feb. 1992, pp. 49–53, Environmental Progress (vol. 11, No. 1).

*Primary Examiner*—Kathryn Gorgos
*Assistant Examiner*—Arun S. Phasge
*Attorney, Agent, or Firm*—Henry P. Sartorio

[57] ABSTRACT

An electrochemical cell for capacitive deionization and electrochemical purification and regeneration of electrodes includes two oppositely disposed, spaced-apart end plates, one at each end of the cell. Two generally identical single-sided end electrodes, are arranged one at each end of the cell, adjacent to the end plates. An insulator layer is interposed between each end plate and the adjacent end electrode. Each end electrode includes a single sheet of conductive material having a high specific surface area and sorption capacity. In the preferred embodiment, the sheet of conductive material is formed of carbon aerogel composite. The cell further includes a plurality of generally identical double-sided intermediate electrodes that are equidistally separated from each other, between the two end electrodes. As the electrolyte enters the cell, it flows through a continuous open serpentine channel defined by the electrodes, substantially parallel to the surfaces of the electrodes. By polarizing the cell, ions are removed from the electrolyte and are held in the electric double layers formed at the carbon aerogel surfaces of the electrodes. As the cell is saturated with the removed ions, the cell is regenerated electrically, thus significantly minimizing secondary wastes.

37 Claims, 16 Drawing Sheets

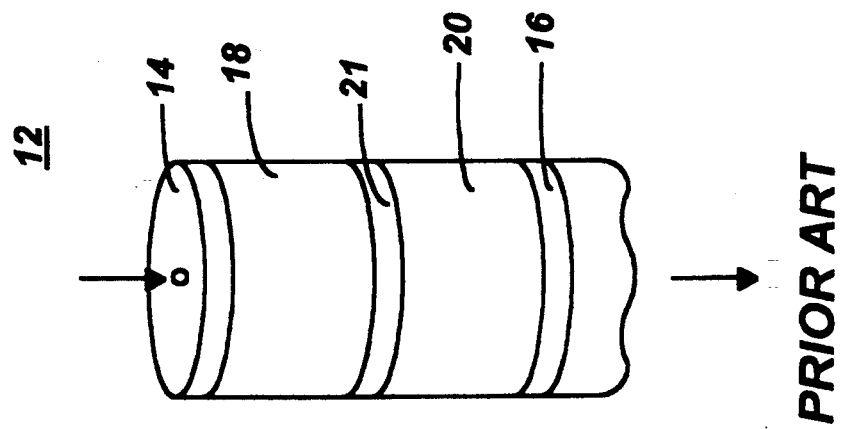
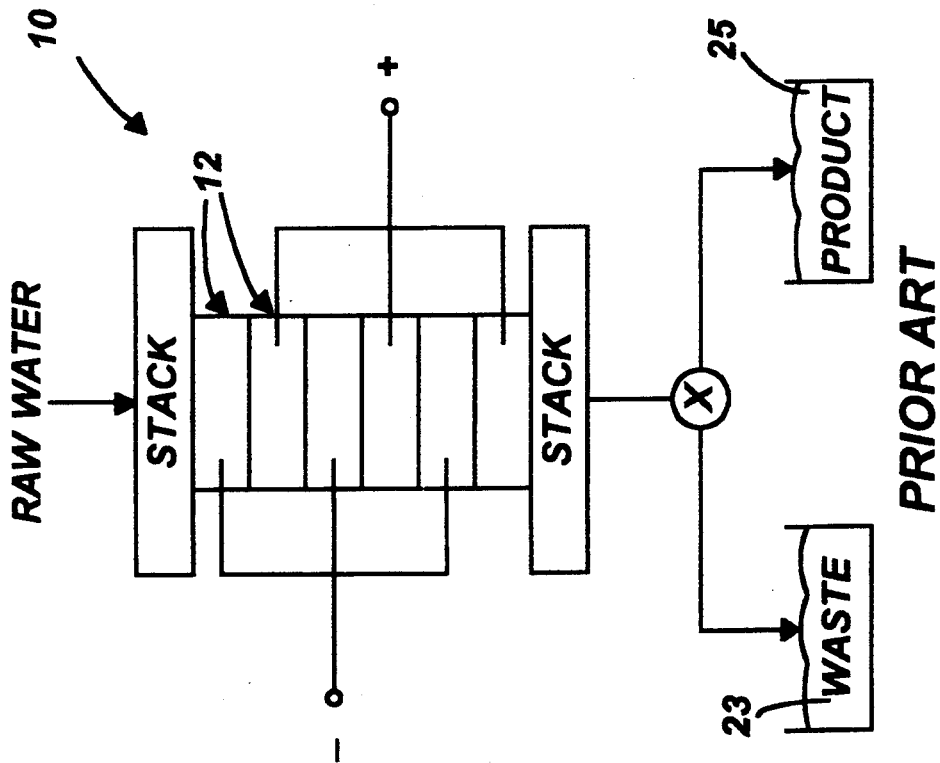
PRIOR ART
FIGURE 2
PRIOR ART
FIGURE 1

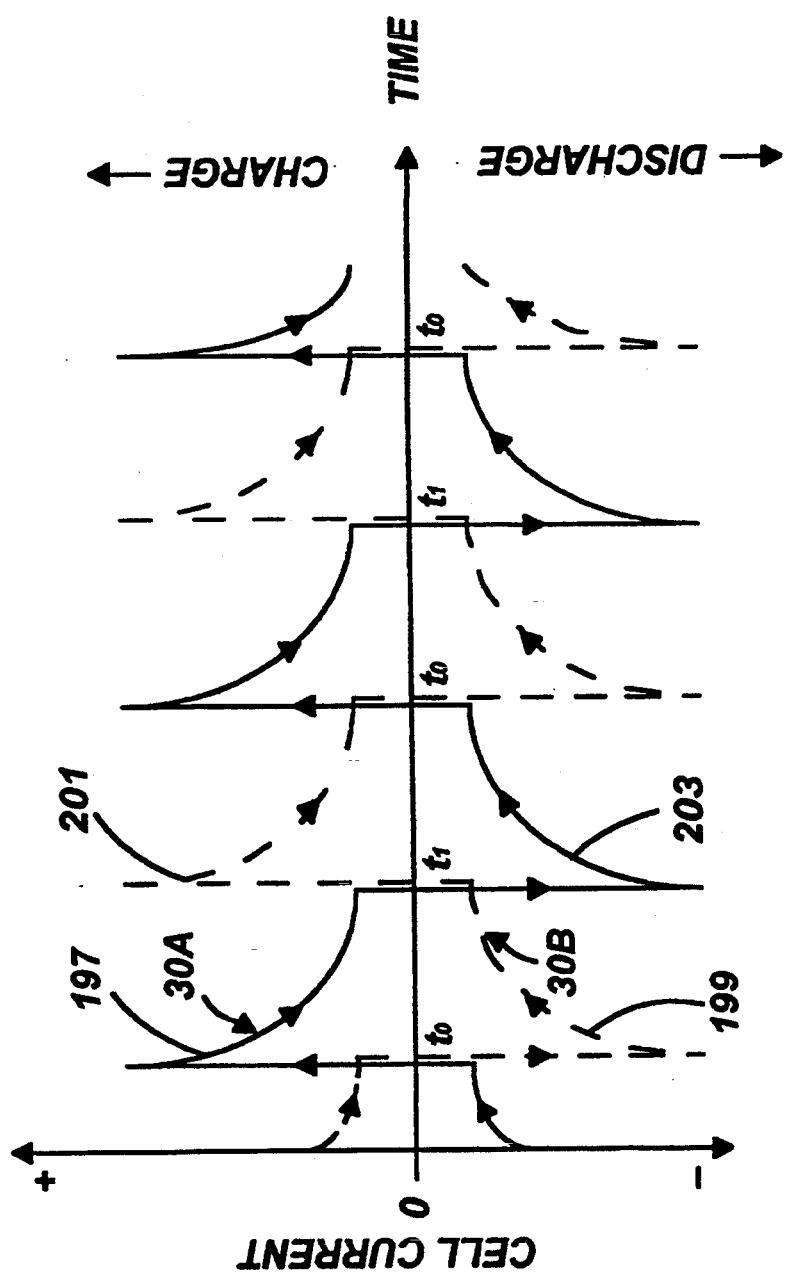

METHOD AND APPARATUS FOR CAPACITIVE DEIONIZATION, ELECTROCHEMICAL PURIFICATION, AND REGENERATION OF ELECTRODES

STATEMENT OF GOVERNMENT RIGHTS

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The present invention is generally directed to the field of electrochemistry, and it more specifically relates to a new separation method and apparatus for removing ions, contaminants and impurities from water and other aqueous process streams, and for placing the removed ions back into solution during regeneration of the apparatus.

2. Background Art

The separation of ions and impurities from electrolytes has heretofore been generally achieved using a variety of conventional processes including: ion exchange, reverse osmosis, electrodialysis, electrodeposition, or filtering. Several other methods have been proposed and address the problems associated with the conventional separation processes. However, these proposed methods have not been completely satisfactory for specific applications nor useful for all applications, and have not met with universal commercial success or complete acceptance. One such proposed ion separation method, which relates to a process for desalting water based on periodic sorption and desorption of ions on the extensive surface of porous carbon electrodes, will be described later in more detail.

The conventional ion exchange process has been used as a means for removing anions and cations, including heavy metals and radioisotopes, from process and waste water in various industries. This process generates large volumes of corrosive secondary wastes that must be treated for disposal through regeneration processes. Existing regeneration processes are typically carried out following the saturation of the columns by ions, by pumping regeneration solutions, such as concentrated acids, bases, or salt solutions through the columns. These routine maintenance measures produce significant secondary wastes, as well as periodic interruptions of the deionization process.

Secondary wastes resulting from the regeneration of the ion exchangers typically include used anion and cation exchange resins, as well as contaminated acids, bases and/or salt solutions. For example, $H_2SO_4$ solutions have been used for the regeneration of cation columns in metal finishing and power industries; and $HNO_3$ solutions have been used for the regeneration of cation columns used in processing nuclear materials.

In some instances, the secondary radioactive wastes are extremely hazardous and can cause serious environmental concerns. For instance, during plutonium processing, resins and solutions of $HNO_3$ become contaminated with $PuO_2^{++}$ and other radioisotopes. In this case, every pound of cation exchange resin requires approximately 100 pounds of 10 wt. % $HNO_3$ and 2 to 3 pounds of rinse water for regeneration. Similarly, every pound of anion exchange resin requires approximately 100 pounds of 10 wt. % NaOH and 2 to 3 pounds of rinse water for regeneration. Given the high and increasing cost of disposal of secondary wastes in mined geological repositories, there is tremendous and still unfulfilled need for reducing, and in certain applications, eliminating the volume of secondary wastes.

Another example is the use of the ion exchange process for industrial purposes, such as in the electroplating and metal finishing industries. A typical electroplating process includes immersing the article to be electroplated in an electroplating bath which contains dissolved metals, such as nickel, cadmium zinc, copper, silver and/or gold, as well as a variety of salts, and then rinsing this article. Once the electroplating process is completed, the plated article is rinsed to remove residual plating solution and associated contaminants. The rinsing process includes hanging the article on a rack above a rinse tank and spraying it with rinse water from spray nozzles around the top of the rinse tank.

The rinse water becomes contaminated, and a major dilemma currently facing the industry relates to the difficulties, cost considerations and the environmental consequences for disposing of the contaminated rinse solution. A typical treatment method for the contaminated rinse water is the ion exchange process.

Other exemplary processes which further illustrate the problems associated with ion exchange include residential water softening and the treatment of boiler water for nuclear and fossil-fueled power plants. At the present time, domestic water softeners use a concentration solution of sodium chloride to regenerate a bed of ion exchange resin. Unfortunately, such water softeners result in a relatively high concentrated solution of sodium chloride in the drinking water produced by the system. Therefore, additional desalination devices, such as reverse osmosis filters are needed to remove the excess sodium chloride introduced during regeneration. It should be noted that people on low-salt diets also require low-salt water. A solution that contains contaminants from the ion exchange resin is produced during regeneration and must be discharged to the sewer.

Boiler water for nuclear and fossil-fueled power plants is treated with ion exchange to remove ionic contaminants such as $Mg^{++}$, $Ca^{++}$, $Cu^{++}$, and $Cl^-$, and is essential for the prevention of pitting, stress corrosion cracking, and scaling of heat transfer surfaces. Such treatment is particularly important on nuclear powered ships and submarines. Another important example is the production of high-purity water for semiconductor processing. Other applications could include the removal of toxic ions, especially those containing selenium, from waters produced by agricultural irrigation.

Therefore, there is still a significant and growing need for a new method and apparatus for deionization and subsequent regeneration, which significantly reduce, if not entirely eliminate secondary wastes in certain applications. This method and apparatus should not require salt additions for ion regeneration in a water softening system, and further should not require additional desalination devices, such as reverse osmosis filters, to remove the excess sodium chloride introduced during regeneration.

Additionally, the new method and apparatus should enable the separation of any inorganic or organic ion or dipole from any ionically conducting solvent, which could be water, an organic solvent, or an inorganic solvent. For example, it should be possible to use such a process to purify organic solvents, such as propylene carbonate, for use in lithium batteries and other energy storage devices. Furthermore, it should be possible to use such a process to remove organic ions, such as formate or acetate from aqueous streams.

The new method and apparatus should further be adaptable for use in various applications, including without limitation, treatment of boiler water in nuclear and fossil power plants, production of high-purity water for semiconductor processing, removal of toxic and hazardous ions from water for agricultural irrigation, and desalination of sea water.

In the conventional reverse osmosis systems, water is forced through a membrane, which acts as filter for separating the ions and impurities from electrolytes. Reverse osmosis systems require significant energy to move the water through the membrane. The flux of water through the membrane results in a considerable pressure drop across the membrane. This pressure drop is responsible for most of the energy consumption by the process. The membrane will also degrade with time, requiring the system to be shut down for costly and troublesome maintenance.

Therefore, there is a need for a new method and apparatus for deionization and ion regeneration, which substitute for the reverse osmosis systems, which do not result in a considerable pressure drop, which do not require significant energy expenditure, or interruption of service for replacing the membrane(s).

The conventional ion separation method relating to a process for desalting water based on periodic sorption and desorption of ions on the extensive surface of porous carbon electrodes is described in the Office of Saline Water Research and Development Progress Report No. 516, March 1970, U.S. Department of the Interior PB 200 056, entitled *The Electrosorb Process for Desalting Water*, by Allan M. Johnson et al., hereinafter referred to as the "Department of the Interior Report" and further in an article entitled *"Desalting by Means of Porous Carbon Electrodes"* by J. Newman et al., in J. Electrochem. Soc.: Electrochemical Technology, March 1971, Pages 510–517, hereinafter referred to as the "Newman Article", both of which are incorporated herein by reference. A comparable process is also described in NTIS research and development progress report No. OSW-PR-188, by Danny D. Caudle et al., *Electrochemical Demineralization of Water with Carbon Electrodes*, May, 1966.

The Department of the Interior Report and the Newman Article review the results of an investigation of electrosorption phenomena for desalting with activated carbon electrodes, and discuss the theory of potential modulated ion sorption in terms of a capacitance model. This model desalination system 10 is diagrammatically illustrated in FIG. 1, and includes a stack of alternating anodes and cathodes which are further shown in FIG. 2, and which are formed from beds of carbon powder or particles in contact with electrically conducting screens (or sieves). Each cell 12 includes a plurality of anode screens 14 interleaved with a plurality of cathode screens 16, such that each anode screen 14 is separated from the adjacent cathode screen 16 by a first and second beds 18, 20, respectively of pretreated carbon powder. These two carbon powder beds 18 and 20 are separated by a separator 21, and form the anode and cathode of the cell 12. In operation, and as shown in FIG. 1, raw water is flown along the axial direction of the cells 12, perpendicularly to the surface of the electrode screens 14, 16, to be separated by the system 10 into waste 23 and product 25.

However, this model system 10 suffers from several disadvantages, among which are the following:

1. The carbon powder beds 18 and 20 are used as electrodes and are not "immobilized". The primary carbon particles and fines, smaller particles generated by erosion of the primary particles, can become readily entrained in the flow, which eventually depletes the carbon bed, reduces the efficiency of the deionization or desalination system 10, and necessitates maintenance.
2. It is significant that raw water must flow axially through these electrode screens 14 and 16, beds of carbon powder 18 and 20, and separators 21, which cause significant pressure drop and large energy consumption.
3. The carbon bed electrodes 18 and 20 are quite thick, and a large potential drop is developed across them, which translates into lower removal efficiency and higher energy consumption during operation.
4. Even though the carbon particles "touch", i.e., adjacent particles are in contact with each other, they are not intimately and entirely electrically connected. Therefore, a substantial electrical resistance is developed, and significantly contributes to the process inefficiency. Energy is wasted and the electrode surface area is not utilized effectively.
5. The carbon beds 18 and 20 have a relatively low specific surface area.
6. The carbon powder bed electrodes 18 and 20 degrade rapidly with cycling, thus requiring continuous maintenance and skilled supervision.
7. The model system 10 is designed for one particular application, namely sea water desalination, and does not seem to be adaptable for use in other applications.

Therefore, there is still a significant unfulfilled need for a new method and apparatus for deionization and regeneration, which, in addition to the ability to significantly reduce if not to completely eliminate secondary wastes associated with the regeneration of ion exchange columns, do not result in a considerable pressure drop of the flowing process stream, and do not require significant energy expenditure. Furthermore, each electrode used in this apparatus should be made of a structurally stable, porous, monolithic solid. Such monolithic electrodes should not become readily entrained in, or depleted by the stream of fluid to be processed, and should not degrade rapidly with cycling. These electrodes should have a very high specific surface area; they should be relatively thin, require minimal operation energy, and have a high removal efficiency. The new method and apparatus should be highly efficient, and should be adaptable for use in a variety of applications, including, but not limited to sea water desalination.

SUMMARY OF THE INVENTION

It is therefore an object of the present invention to provide a new separation process and apparatus for removing ions, contaminants, impurities and like matters from water and other aqueous process streams, and for subsequently electrically placing the removed ions back into a solution during the regeneration process.

It is another object of the present invention to provide a new separation process and apparatus which address the concerns associated with conventional separation devices, and which provide adequate solutions thereto.

It is yet another object of the present invention to provide a new separation process and apparatus which capacitively deionize streams of electrolyte, and which regenerate the apparatus electrically.

It is still another object of the present invention to provide a new separation process and apparatus which do not utilize chemical regeneration processes, and thus significantly reduce, and in certain application completely eliminate secondary wastes associated with the operation of ion exchange resins.

It is another object of the present invention to provide a new separation process and apparatus which do not result in a considerable pressure drop of the electrolyte.

It is still another object of the present invention to provide a new separation process and apparatus that are more energy efficient than conventional processes.

It is a further object of the present invention to provide a new separation apparatus comprising electrodes which do not become readily entrained in, or depleted by the electrolyte, and which do not degrade rapidly with cycling.

It is yet another object of the present invention to provide a new separation apparatus comprising electrodes which have a significantly high specific surface area and a high removal efficiency, which are relatively thin, and which require minimal operation energy.

It is still another object of the present invention to provide a new separation process and apparatus which are highly efficient and adaptable for use in a variety of applications, including, but not limited to domestic water softening, industrial water softening, waste water purification, and sea water desalination.

It is a further object of the present invention to provide a new separation process and apparatus which do not require salt additions for ion regeneration in a water softening system, and which further do not require additional desalination devices, such as reverse osmosis filters to remove the excess sodium chloride introduced during regeneration.

It is yet another object of the present invention to provide a new separation process which is chemically stable, thus preventing the novel apparatus from prematurely degrading.

It is still another object of the present invention to provide a new separation process and system with continuous deionization and regeneration capability.

It is yet another object of the present invention to provide a new separation method and system with selective and progressive deionization and regeneration capability.

In the preferred embodiment, the new separation process is used for the deionization of water and the treatment of aqueous wastes. This new process will also be referred to as capacitive deionization. Unlike the conventional ion exchange processes, no chemicals, whether acids, bases, or salt solutions, are required for the regeneration of the system; instead, electricity is used.

A stream of electrolyte to be processed, which contains various anions and cations, electric dipoles, and/or suspended particles is passed through a stack of electrochemical capacitive deionization cells. Each of these cells includes numerous carbon aerogel electrodes having exceptionally high specific surface areas (for example, 400–1000 $m^2/gm$). By polarizing the cell, non-reducible and non-oxidizable ions are removed from the fluid stream electrostatically and held in the electric double layers formed at the surfaces of the electrodes. Some metal cations are removed by electrodeposition. Electric dipoles also migrate to and are trapped at the electrodes. Small suspended particles are removed by electrophoresis. Therefore, the fluid stream leaving the cell is purified.

In conventional desalting and purification processes, such as evaporation and reverse osmosis, energy is expanded removing water from salt and other impurities. Consequently, the required energy is great. According to the present inventive capacitive deionization process, energy is expanded using electrostatics to remove salt and other impurities from the fluid, and, as a result, is orders-of-magnitude more energy efficient than conventional processes. Furthermore, the pressure drop in the capacitive deionization cells is dictated by channel flow between parallel surfaces of monolithic, microporous solids (i.e., the electrodes), hence, it is insignificant compared to that needed to force water through the permeable membrane required by the reverse osmosis process.

One of the features of the inventive separation system is that no expensive ion exchange membranes are required for the separation of the electrodes. All the anodes and cathodes of the electrode pairs are connected in parallel. The present system is modular, and can be readily expanded to include 96 electrode pairs (192 electrodes) with a total anode or cathode surface area of approximately $2.7 \times 10^8$ $cm^2$. Ultimately, the system capacity can be increased to any desired level by expanding the cell(s) to include a greater number of electrode pairs. The conductivity and the pH of the inlet and exit streams are continuously monitored.

Initial experiments have been conducted with complete recycle (batch mode), or with no recycle (continuous mode). In some of these experiments, sodium chloride solution was used. The conductivity of this solution was comparable to hard tap water and was reduced to less than 85 percent of its initial level by capacitive deionization. Greater separation is possible. In the continuous mode of operation, which was possible before saturation of the stack, it was possible to remove over 97% of the salt from water with an initial conductivity greater than 100 micromhos. With sufficient electrode capacity, the same or greater removal is possible at much higher ion concentrations.

Some advantages of the present invention include, but are not limited to the following:

1. Unlike the conventional osmosis process where water is forced through a membrane by pressure gradient, and unlike the conventional ion exchange process and the process described in the Newman Article and the Department of Interior Report, where fluid is flown through a packed bed, the present separation methods and systems do not require the electrolyte to flow through any porous media such as membranes or packed beds. In the present system, electrolyte flows in open channels formed between two adjacent, planar electrodes, which are geometrically parallel. Consequently, the pressure drop is much lower than conventional processes. The fluid flow can be gravity fed through these open channels, or alternatively, a pump can be used.

2. The present system does not require membranes, which are both troublesome and expensive, which rupture if overpressured, which add to the internal resistance of the capacitive cell, and which further reduce the system energy efficiency. This feature represents a significant advantage over the conventional reverse osmosis systems which include water permeable cellulose acetate membranes, and over the electrodialysis systems which require expensive and exotic ion exchange membranes.

3. The electrodes in the present system are composed of immobilized sorption media, such as monolithic carbon aerogel which is not subject to entrainment in the flowing fluid stream. Thus, material degradation due to entrainment and erosion is considerably less than in conventional packed carbon columns. This feature represents yet another significant advantage over the systems described in the Department of the Interior Report and the Newman Article where activated carbon is lost from the bed over the conventional ion exchange systems where ion exchange resin is lost from the beds.

4. The present systems and methods are inherently and greatly energy efficient. For instance, in both evaporation and reverse osmosis processes, water is removed from salt, while in the present systems, salt is removed from water, thus expending less energy.

5. The present systems and methods present superior potential distribution in the thin sheets of carbon aerogel. Unlike the deep, packed carbon beds used in the electrosorb process discussed in the Department of Interior Report and in the Newman Article, most of the carbon aerogel is maintained at a potential where electrosorption is very efficient. In deep, packed carbon beds, the potential drops to levels where the electrosorption process is not very effective. Furthermore, the specific surface area of the sorption media used in the present process is significantly greater than that of carbon powder. This feature also contributes significantly to overall process efficiency.

Additionally, the present separation processes and systems have several important applications, among which are the following:

1. Removal of various ions from waste water without the generation of acid, base, or other similar secondary wastes. This application may be especially important in cases involving radionuclides, where the inventive capacitive deionization process could be used to remove low-level radioactive inorganic materials.

2. Treatment of boiler water in nuclear and fossil power plants. Such treatment is essential for the prevention of pitting, stress corrosion cracking, and scaling of heat transfer surfaces. Such a process may be particularly attractive for nuclear powered ships and submarines where electrical power is readily available and where there are space limitations, thereby restricting the inventory of chemicals required for regeneration of ion exchange resins.

3. Production of high-purity water for semiconductor processing. In addition to removing conductivity without the addition of other chemical impurities, the system is capable of removing small suspended solids by electrophoresis. Furthermore, the organic impurities chemisorb to the carbon.

4. Electrically-driven water softener for homes. The present system would soften home drinking water without the introduction of sodium chloride. At the present time, domestic water softeners use sodium chloride to regenerate a bed of ion exchange resin. Downstream of the ion exchanger, reverse osmosis has to be used to remove the sodium chloride introduced during regeneration. People on low-salt diets require low-salt water. The present capacitive deionization system does not require salt additions for regeneration, does not have to be followed by a reverse osmosis system, and will also remove hazardous organic contaminants and heavy metals from the water.

5. Removal of salt from water for agricultural irrigation. The energy efficiency of such a process and the lack of troublesome membranes could make such a process a contender for treating water for irrigation purposes. Solar energy could be used to power the low-voltage, low-current capacitive deionization plants.

6. Desalination of sea water. Such an application can be accomplished using the present separation method and system.

By using the separation systems according to the present invention, it is now possible to remove organic and inorganic contaminants and impurities from the liquid streams by the following physiochemical processes: the reversible electrostatic removal of organic or inorganic ions from water or any other dielectric solvent; the reversible or irreversible removal of any organic or inorganic impurity by any other adsorption process, including but not limited to underpotential metal deposition, chemisorption, and physisorption; the removal of any organic or inorganic impurity by electrodeposition, which could involve either electrochemical reduction or electrochemical oxidation; and the electrophoretic deposition and trappings of small suspended solids, including but not limited to colloids, at the surface of the electrodes. It is recognized that induced electric dipoles will be forced to the electrode surfaces by the imposed electric field.

More specific applications for the inventive system and process include any application where the capacitive deionizer is used to assist a gas scrubbing column; for example, if $CO_2$ were removed from a gas stream into an aqueous stream, it would convert into $HCO_3^-$ and $CO_3^{2-}$. These ions could be removed from the scrubbing solution by capacitive deionization. Such applications include any large scale parallel use of the capacitive deionizer to assist in load leveling applications since it is recognized that the present invention can simultaneously serve as an energy storage device. Other applications include analytical instruments that combine the principles of capacitive deionization and ion chromatography, and chromatographic instruments based upon ion adsorption on carbon aerogel electrodes, either monolithic or powder beds.

Briefly, the above and further features and advantages of the present invention are realized by a new electrochemical cell for capacitive deionization and electrochemical purification and regeneration of electrodes. The cell includes two oppositely disposed, spaced-apart end plates, one at each end of the cell, as well as two generally identical single-sided end electrodes, that are arranged one at each end of the cell, adjacent to the end plates. An insulator layer is interposed between each end plate and the adjacent end electrode.

Each end electrode includes a single sheet of conductive material having a high specific surface area and sorption capacity. In the preferred embodiment, the sheet of conductive material is formed of carbon aerogel composite. The cell further includes a plurality of generally identical double-sided intermediate electrodes that are equidistally separated from each other, between the two end electrodes. As the electrolyte enters the cell, it flows through a continuous open serpentine channel defined by the electrodes, substantially parallel to the surfaces of the electrodes. By polarizing the cell, ions are removed from the electrolyte and are held in the electric double layers formed at the carbon aerogel surfaces of the electrodes. As the cell is saturated with the removed ions, the cell is regenerated electrically, thus significantly minimizing secondary wastes. Additional embodiments of the present will hereafter be described in detail.

BRIEF DESCRIPTION OF THE DRAWINGS

The above and other features of the present invention and the manner of attaining them, will become apparent, and the invention itself will be best understood, by reference to the following description and the accompanying drawings, wherein:

FIG. 1 is a diagrammatic view of a model desalination system according to the prior art;

FIG. 2 is an enlarged schematic, isometric, elevational view of a cell used in the model desalination system of FIG. 1;

DETAILED DESCRIPTION OF THE PREFERRED EMBODIMENTS

Figure 3:
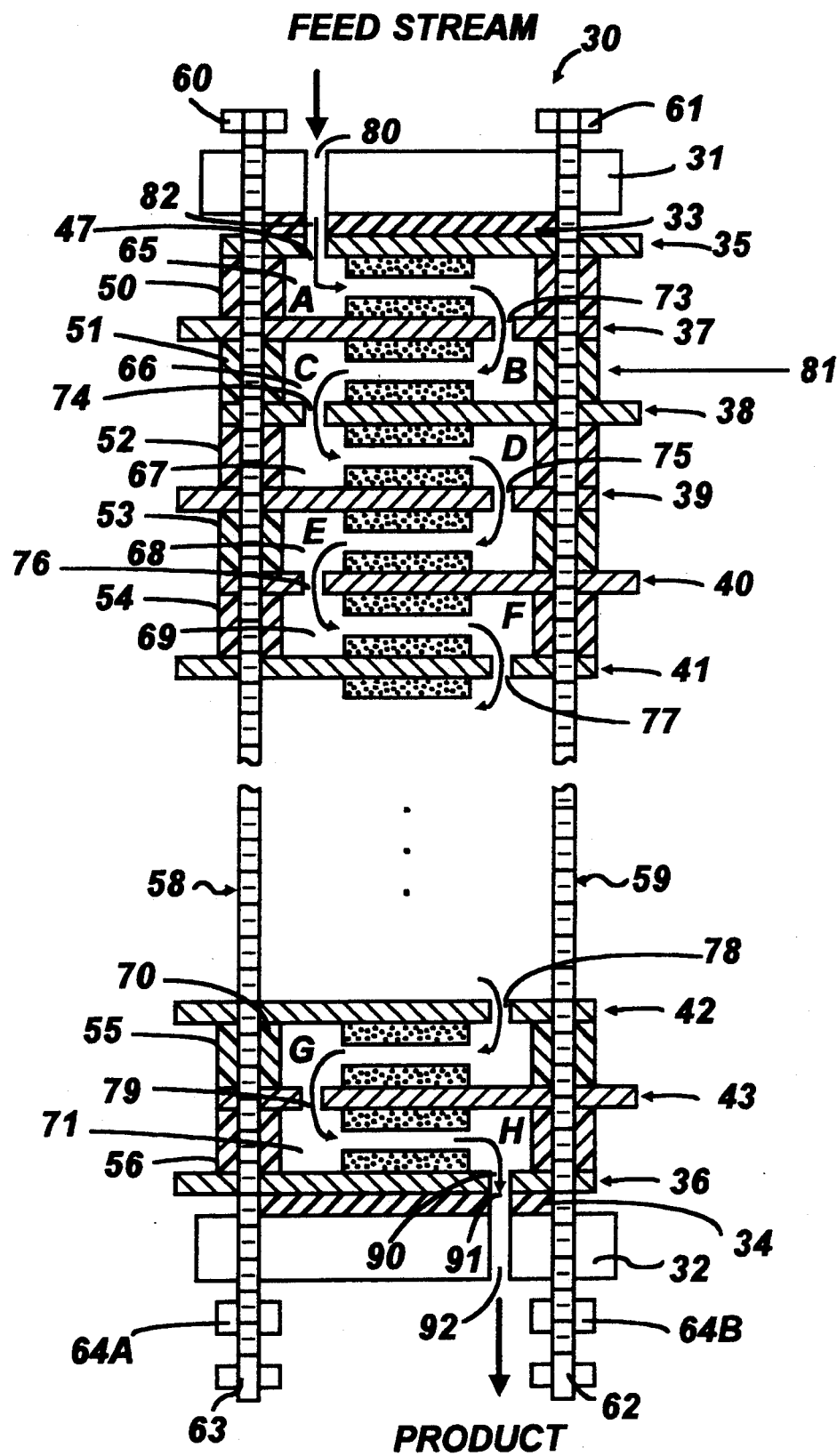
FIG. 3 is a schematic, sectional, elevational view of an electrochemical cell which is constructed according to the present invention.

Referring now to the drawings, and in particular to FIG. 3 thereof, there is illustrated an electrochemical cell 30 which is constructed according to the present invention. The cell 30 generally includes two oppositely disposed, spaced-apart end plates 31 and 32, one at each end of the cell 30, and two generally identical single-sided end electrodes 35, 36, one at each end of the cell 30, adjacent to the end plates 31 and 32, respectively. An insulator layer 33 is interposed between the end plate 31 and the end electrode 35. Similarly, an insulator layer 34 is interposed between the end plate 32 and the end electrode 36. Each single-sided electrode 35, 36 includes a single sheet of carbon aerogel composite bonded to one side of a titanium sheet with a conductive epoxy. Other appropriate bonding material can alternatively be used.

A plurality of generally identical double-sided intermediate electrodes (i.e., 37 through 43) are spaced-apart and equidistally separated from each other, between the two end electrodes 35, 36. Each double-sided electrode, i.e., 37, includes two sheets of carbon aerogel composite bonded to both sides of a titanium sheet with conductive epoxy. While FIG. 3 illustrates only seven double sided intermediate electrodes 37 through 43, it should become apparent to those skilled in the art that a different number of intermediate electrodes can alternatively be used without departing from the scope of the present invention. For instance, it would be possible to expand the capacity of the cell 30 to accommodate at least 192 intermediate electrodes, such that the total anode (or cathode) surface area is approximately $2.7 \times 10^8$ cm$^2$. Ultimately, the system could be expanded to include an unlimited number of electrode pairs.

The end electrodes 35, 36 and the intermediate electrodes 37 through 43 are generally similar in design, construction and composition, with the difference that each intermediate electrode has two sheets of carbon aerogel composite bonded to both sides of a titanium sheet with conductive epoxy, whereas each end electrode has only one sheet of carbon aerogel composite bonded to one side of a titanium sheet with conductive epoxy. It is recognized that other porous conductive, monolithic materials can be used in lieu of the carbon aerogel composite. For brevity, only one single-sided end electrode, i.e., 35, will now be described in more detail in connection with FIGS. 4A and 4B.

Figure 4A:
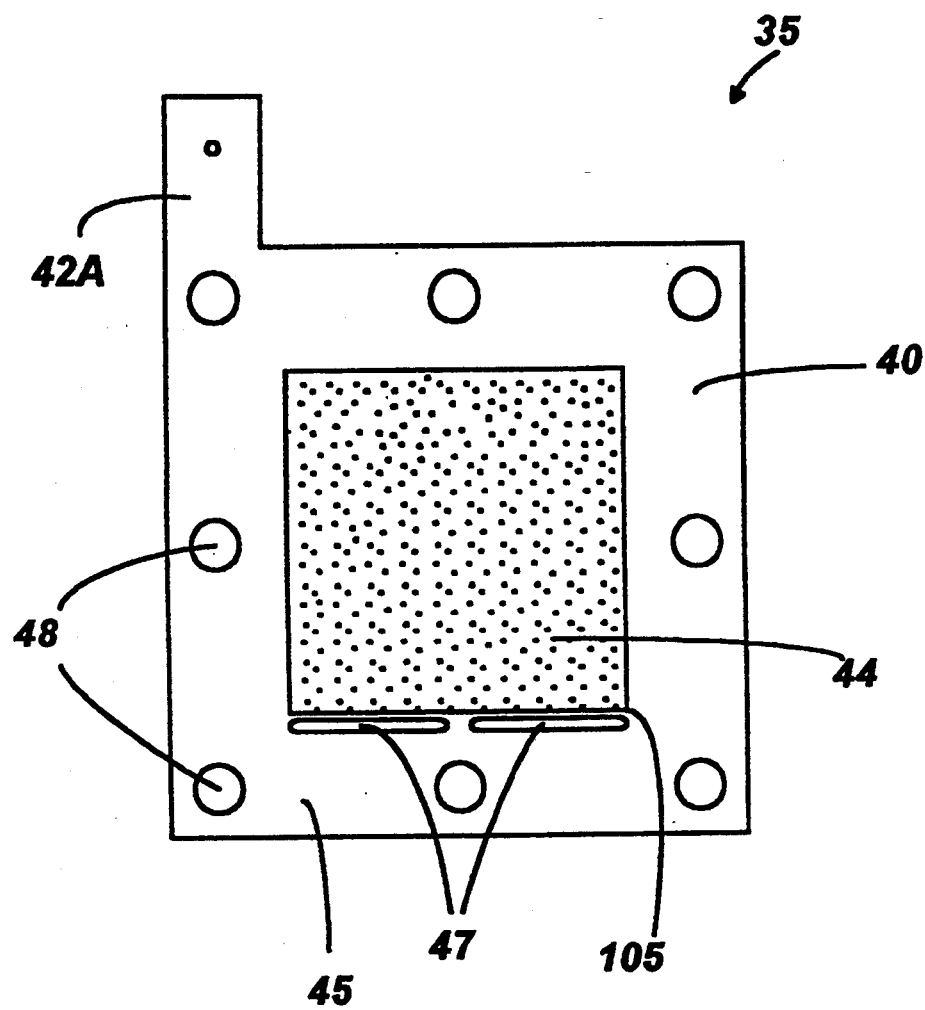
FIG. 4A is a greatly enlarged top plan view of a capacitive electrode according to the present invention, adapted for use in the electrochemical cell of FIG. 3.

FIG. 4A is a greatly enlarged top plan view of the end electrode, which includes a generally flat, thin rectangularly shaped, corrosion resistant, metallic (i.e., titanium) sheet, structural support 40. A tab 42A extends integrally from one side of the structural support 40, for connection to the appropriate pole of a D.C. power source (not shown). A thin sheet 44 of high specific area, porous, conductive, monolithic material (i.e., carbon aerogel composite) is bonded to the surface of the structural support 40, and is suitable to be either a cathode or an anode. In this particular example, it will be presumed that the end electrode 35 is an anode. The structural support 40 further includes a series of generally identical apertures 47 for providing a passage to the electrolyte, through the end electrode 35.

In the preferred embodiment, the thin layer of high specific area material 44 is composed of a composite material formed by impregnating a carbon cloth with carbon aerogel, wherefore, the thin layer 44 will also be referred to as carbon aerogel composite electrode 44. The new use of this carbon aerogel composite electrode 44 relies primarily on the unique open-cell nanostructure of the carbon aerogel material, including its interconnected porosity, ultrafine pore sizes and huge surface area. This carbon aerogel composite material is described in more detail in an article entitled *Carbon Aerogel Composite Electrodes*, by Joseph Wang et al., in Anal. Chem. 1993, vol. 65, pages 2300–2303, and in several articles and patents authored by Richard W. Pekala et al., such as U.S. Pat. No. 5,260,855 entitled Supercapacitors Based on Carbon Foams, which are incorporated herein by reference.

Carbon aerogels were developed at Lawrence Livermore Notional Laboratory, and are synthesized by the polycondensation of resorcinol and formaldehyde (in a slightly basic medium), followed by supercritical drying and pyrolysis (in an inert atmosphere). This fabrication process results in unique open-cell carbon foams that have high porosity, high surface area (400–1000 $m^2/g$), ultrafine cell/pore sizes (less than 50 nm), and a solid matrix composed of interconnected colloidal-like particles or fibrous chains with characteristic diameters of 10 nm. The porosity and surface area of aerogels can be controlled over a broad range, while the pore size and particle size can be tailored at the nanometer scale. The carbon aerogels further offer both low density and ultrasmall cell size.

The use of the carbon aerogel composite electrode 44 presents a significant improvement over conventional devices, since in these latter devices only part of the specific area is effective for removing ions, and the remaining area is not effective because of the potential gradients across the electrodes. By using thin sheets of carbon aerogel composite as electrodes 44, substantially the entire surface area of these monolithic microporous electrodes is effective in the removal of ions, due to the desirable potential distribution in the aerogel.

While the best mode of the present invention utilizes thin sheets of carbon aerogel composite as electrodes, it should be apparent to those skilled in the art that beds of carbon aerogel particles can alternatively be used to form electrodes. Such beds of carbon aerogel particles have much higher specific area and sorption capacity than beds of conventional carbon powder, and therefore they are superior electrodes for capacitive deionization.

Figure 4B:
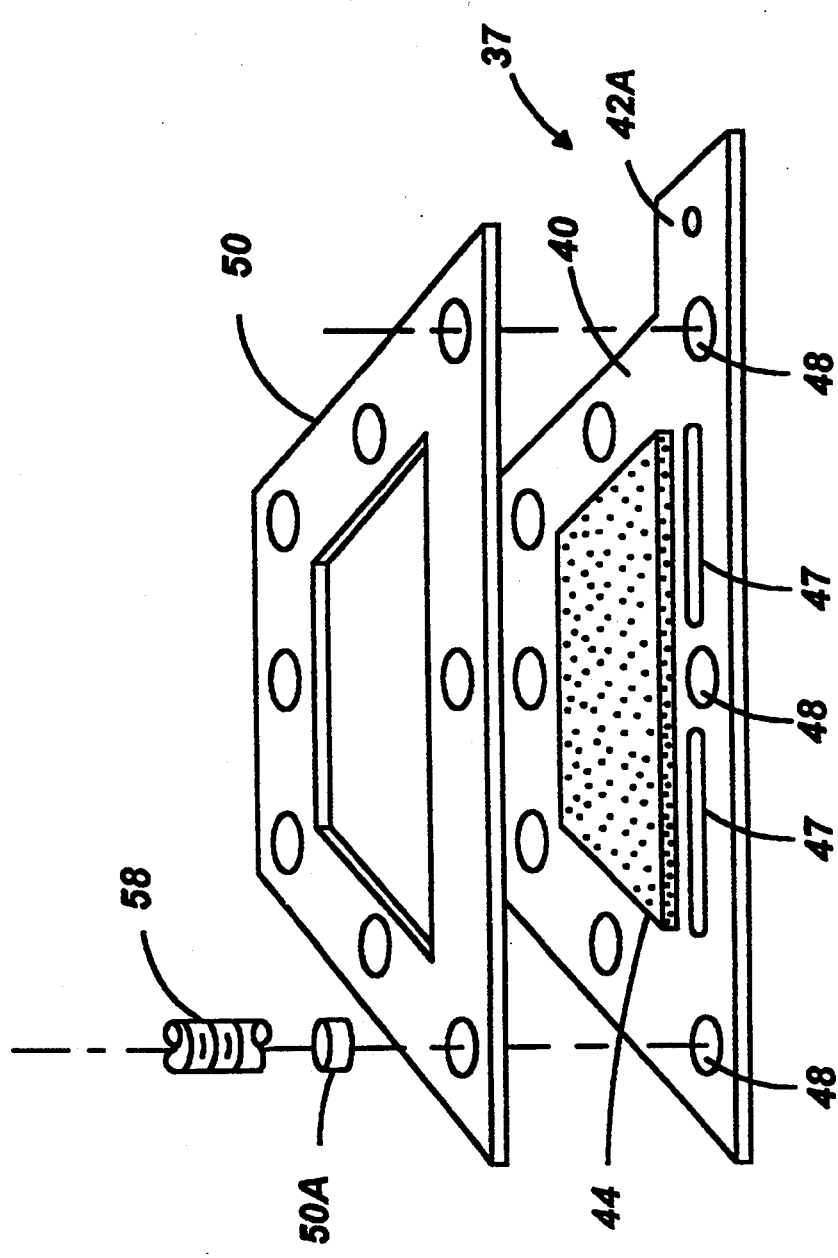
FIG. 4B is a greatly enlarged exploded view of a rubber gasket used in conjunction with the capacitive electrode of FIG. 4A.

Returning now to FIG. 3, the end electrodes 35, 36 and the adjacent intermediate electrodes 37 through 43 are separated by means of thin sheets of insulating material, such as rubber gaskets 50 through 56. Each gasket has a large, square aperture in the center to accommodate adjacent carbon aerogel composite electrodes 44. As shown in FIGS. 4A and 4B, the structural support 40 includes a plurality of peripheral holes 48, such that when the cell 30 is to be assembled, the peripheral holes 48 are coaligned with corresponding peripheral holes in the insulation layers 33, 34 and the rubber gaskets 50 through 56, and a plurality of threaded rods 58, 59 are inserted through these coaligned holes, and are tightened by conventional means, such as nuts 60 through 63. Non-compressible, insulating, hollow, cylindrical spacers or compression rings 50A can be inserted in the peripheral holes of the rubber gaskets 50 through 56, and used to control the spacing of adjacent electrodes. A plurality of compression sleeves, i.e., 64A, 64B can be added to provide additional force for sealing.

While only two threaded rods 58, 59 are shown in FIG. 3 for illustration purpose, in this particular example, eight threaded rods are used to tighten the cell 30 to a leak proof state. These eight rods are designed to fit through the eight peripheral holes 48 in the structural support 40, as well as through the corresponding peripheral holes in the rubber gaskets 50 through 56 fitted with hollow-cylindrical spacers 50A (FIG. 4B).

Once the cell 30 is assembled, a plurality of chambers 65 through 71 are formed between the end and intermediate electrodes 35 through 43. These chambers 65 through 71 are adapted to fluidly communicate with each other via a plurality of apertures 73 through 79 in the structural supports of the intermediate electrodes 37 through 43, respectively. These apertures 73 through 79 are not coaligned, and may be either holes or slits. They are so positioned so that the fluid path therethrough, within the chambers 65 through 71, is forced to flow across all the exposed surfaces of the carbon aerogel composite electrodes 44. Referring to FIG. 3, the fluid first flows from left-to-right, then from right-to-left, an so on.

In operation, and merely for illustration purpose, the anodes and the cathodes of the cell 30 are interleaved in an alternating way. In this respect, every other electrode is an anode, starting with the end electrode 35, and ending with the intermediate electrode 43, and the remaining intermediate electrodes 37, 39, 41, 42 and the end electrode 36 are cathodes. As such, each pair of adjacent electrodes (anode and cathode) forms a separate capacitive deionization/regeneration unit.

The stream of raw fluid or electrolyte to be processed enters the cell 30 through a plurality of superposed, coaxially registered, generally circularly or rectangularly shaped openings, including an aperture 80 in the end plate 31, one or more apertures 82 in the insulation layer 33, and the apertures 47 in the end electrode 35. The fluid flows through the first chamber 65 as indicated by the arrow A, substantially parallel to the electrode surface. By polarizing the first deionization/regeneration unit, ions are removed from the fluid stream electrostatically, and are held in the electric double layers formed at the carbon aerogel surfaces of the electrodes 35 and 37. This will purify the fluid stream, at least partially.

The fluid stream then flows through the aperture 73 into the next chamber as indicated by the arrow B, where additional ions are removed by the polarization of the second deionization/regeneration unit 81 formed by the intermediate electrodes 37 and 38, thus further purifying the fluid stream. The fluid stream continues to travel through the remaining deionization/regeneration units, as indicated by the arrows C through G, and is progressively purified. Thereafter, as indicated by the arrow H, the purified fluid stream exits the cell 30 via a plurality of coaxially aligned apertures 90, 91, 92 in the end electrode 36, insulator layer 34, and the back plate 32, respectively.

The fluid stream leaving the cell 30 is purified since the contamination ions have been removed and collected by the cell 30. It should also become clear that one important characteristic of the novel configuration of the cell 30 is that the fluid stream does not flow through the porous electrodes, but rather in an open channel, with a relatively low pressure drop, and with minimal energy consumption for pumping. The energy expended to operate the cell 30 is minimal. In this respect, the fluid stream does not necessarily need to be pressurized by a pump to cause it to flow through the cell 30; gravity can be used, if desired.

Also, if the inventive deionization process were used for water desalination, the energy expended is that which is necessary to remove salt from water, whereas in conventional desalting processes, such as evaporation and reverse osmosis, the energy is expended to remove the water from salt. As a result, the present process is orders-of-magnitude more energy efficient than conventional processes.

Additionally, the pressure drop in the capacitive deionization cell 30 is insignificant compared to that needed for reverse osmosis. Also, contrary to conventional deionization processes, the electrodes have a very high and immobilized specific surface area and a high removal efficiency, and the carbon aerogel particles are not entrained by the fluid stream.

As the capacitive deionization cell 30 is saturated with the removed ions, the capacitive units become fully charged, and a sensor (not shown) indicates that such condition has been reached, and that the cell 30 is ready for regeneration. Contrary to conventional chemical regeneration processes, the present regeneration process is carried out electrically, thus eliminating the secondary wastes. The regeneration process takes place by disconnecting the power supply, by interconnecting the anodes and the cathodes, by electrically discharging all electrodes 35 through 43, and by flowing a suitable fluid stream of water or another suitable solution through the cell 30, along the same path described above in connection with the deionized stream of raw fluid. As a result, the capacitive units are discharged through, and release the previously removed ions into the flowing fluid stream, until the cell 30 is fully regenerated. At which time, the regeneration process is stopped and the deionization process restarts. The timing control of the deionization-regeneration process could be manual or automated.

Figure 5:
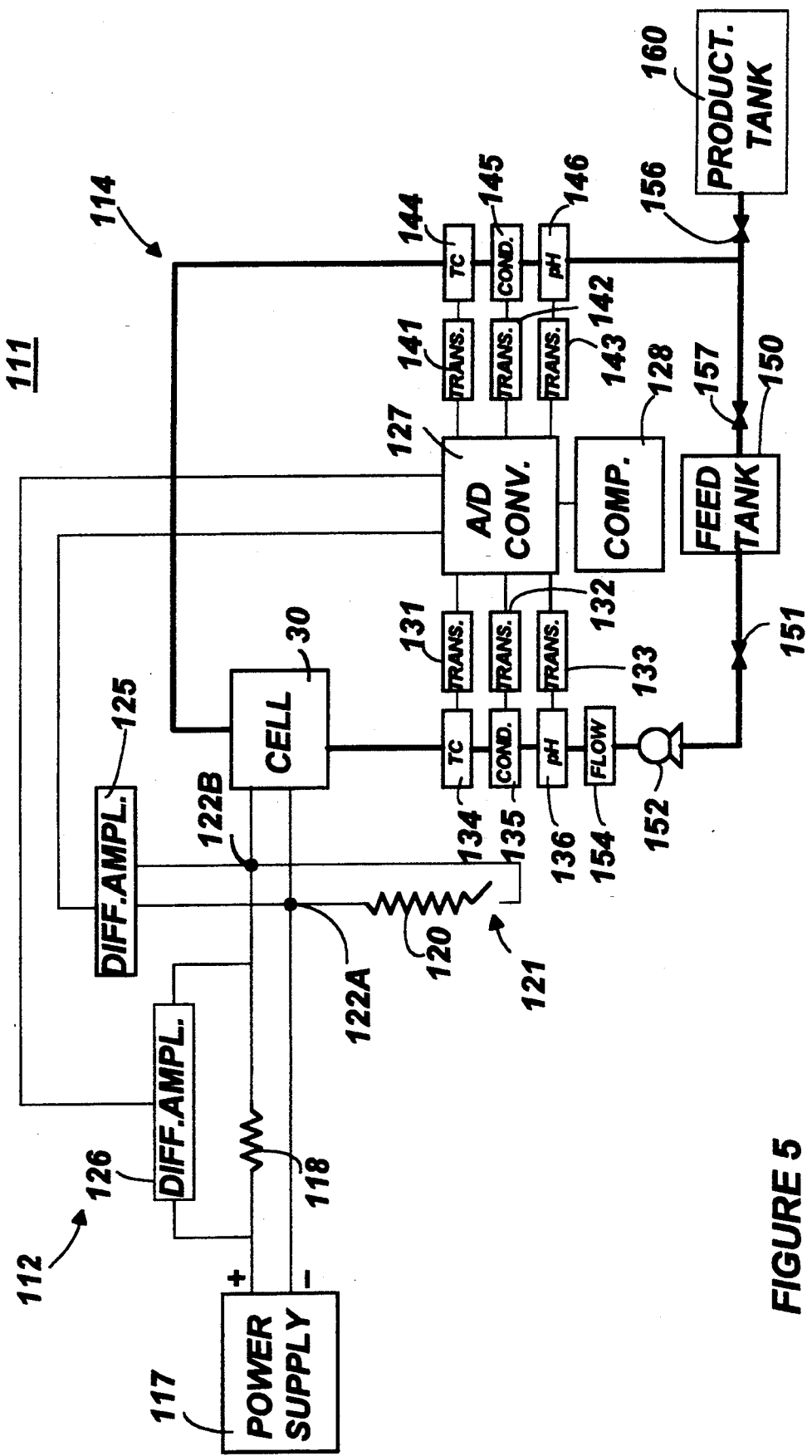
FIG. 5 is a block diagram of a first embodiment of a capacitive deionization-regeneration system using one electrochemical cell shown in FIG. 3.
Figure 7:
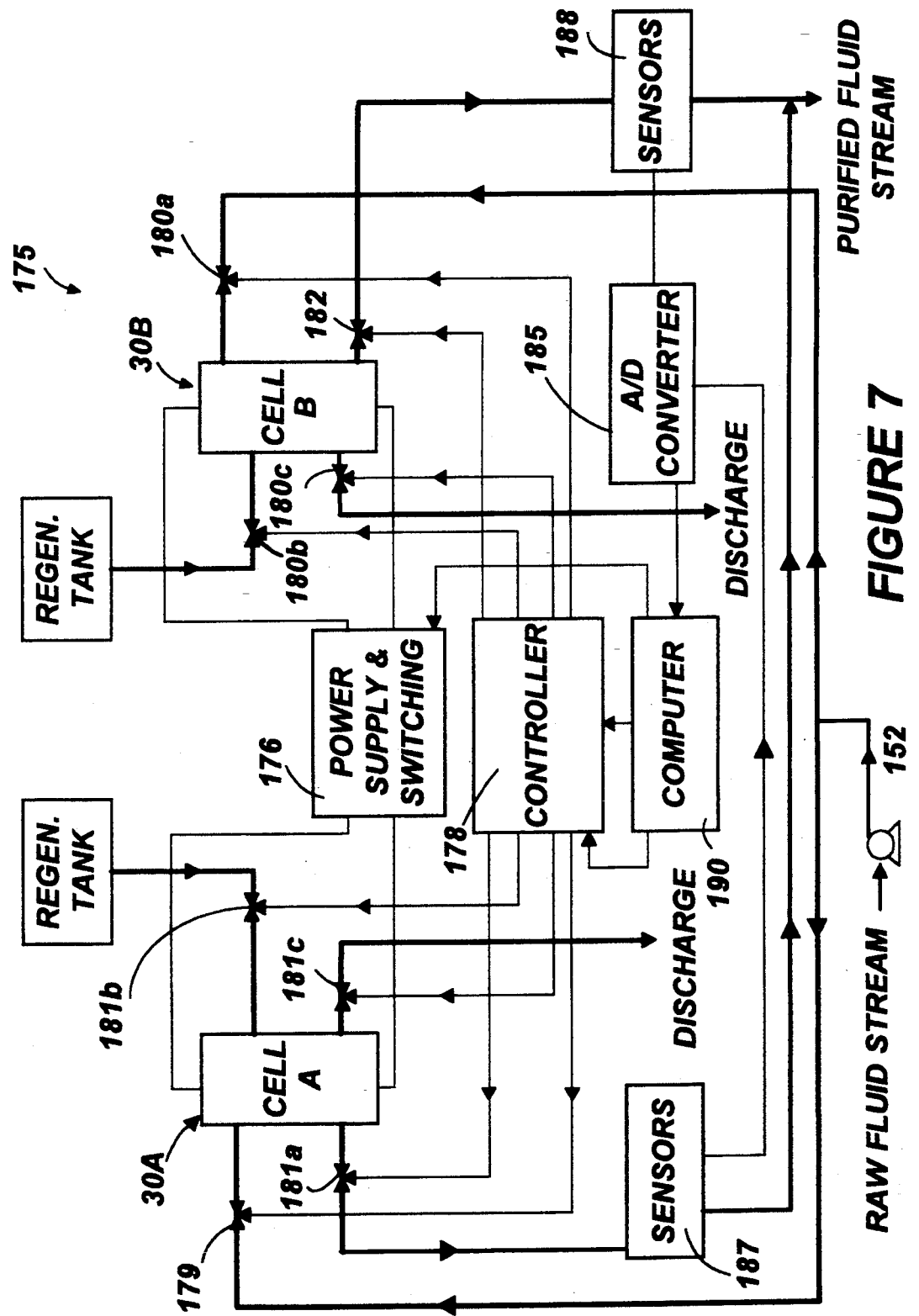
FIG. 7 is a block diagram of a second embodiment of the capacitive deionization-regeneration system using two parallel electrochemical cells, each formed of stacks of numerous electrodes, shown in FIG. 3.

Considering now the components of the cell 30 in more detail, the overall shape and dimensions of the cell 30 are determined by the mode of use and application of the capacitive deionization systems 111 and 175 illustrated in FIGS. 5 and 7, respectively. In the preferred embodiment, the end plates 31 and 32 are identical, rectangularly shaped, and made of 316 stainless steel or another appropriate corrosion resistant alloy. The end plates, unlike the electrodes, are not polarized. However, it should become clear that other shapes are also contemplated by the present invention. For instance, if the cell 30 were cylindrically shaped, the end plates 31 and 32 are circular, or if the cell 30 were conically shaped, one of the end plates 31, 32 can have a smaller size than the other plate, and the size of the electrodes therebetween gradually increases from one end plate to the other.

The insulator layers 33 and 34, as well as 50 through 56 are preferably made of an elastic, compressible, insulating, non-leachable material. Foe example, Teflon, Viton, Neoprene and similar materials are suitable materials for specific applications.

However, other suitable materials are also contemplated by the present invention. The structural supports 40 (FIGS. 4A, 4B) of the end electrodes 35, 36 and the intermediate electrodes 37 through 43 are preferably made of titanium, or, alternatively they can be selected from a suitable group of materials such as coated, corrosion-resistant, iron-chromium-nickel based alloys. Suitable coatings include gold, platinum, iridiun, platinum-iridium alloys, or other similarly corrosion resistant materials.

In one example, the back plates are similarly sized and rectangularly shaped, and have the following dimensions: length 8.38 cm; width 7.87 cm; and thickness 0.16 cm. However, other dimensions can alternatively be used. The tab 42A extends integrally from the structural support 40, and is generally, but not necessarily rectangularly shaped. In the above example, the tab 42A has the following dimensions: length 1.78 cm; width 2.03 cm; and thickness 0.16 cm. This tab 42A is used to make electrical connection with the electrode.

As shown in FIGS. 4A and 4B, the structural support 40 includes a plurality of (in this example eight) peripheral holes 48 through which the threaded rods, i.e., 58, 59 pass, for aligning the electrodes 35 through 43. Several elongated apertures 47 are shown co-aligned outside, along, and adjacent to one side 105 of the sheets of aerogel carbon composite 44. These apertures 47 are sized so as to distribute the flow uniformly across the sheet of carbon aerogel composite with minimal pressure drop. It should also become clear that the number, position and size of these apertures 47 can vary with the desired mode of use and application of the cell 30.

Considering now the carbon aerogel composite electrode 44 in greater detail in connection to FIGS. 4A and 4B, it is shown as having a square shape, and as being centrally positioned relative to the structural support 40. In the present example, the carbon aerogel composite electrode 44 has a side dimension of 6.86 cm, a projected area of 23.5298 cm$^2$, and a thickness of about 0.0127 cm. Other shapes of the electrode 44 are also contemplated by the present invention. For instance, the electrode 44 can be circular, rectangular, or triangular.

While, as described above, the electrode 44 is preferably made of carbon aerogel, composite, any monolithic, porous solid that has sufficient electrical conductivity and corrosion resistance (chemical stability) to function as an electrode, can alternatively be used. Such alternative materials include porous carbon electrodes typically used in fuel cells, reticulated vitreous carbon foams, porous metallic electrodes made by powder metallurgy, porous electrodes made by microfabrication techniques, including photolithography, electroforming, physical vapor deposition (evaporation, sputtering, etc.) and etching, and conductive sponges of any type.

The electrode 44 could also be fabricated as a packed bed of carbon aerogel particles, having significantly higher specific surface area than the conventional packed carbon bed described in the Department of Interior Report and the Newman Article discussed above. This design offers the advantage of greatly enhanced capacity for electrosorption of ions, adsorption of organics, and capture of fine particles, but would require flow through porous media.

In the example illustrated in FIG. 3, the chambers 65 through 71 have a volume of about 300 ml, which corresponds to the minimum possible liquid volume required for regeneration. In other embodiments, the chambers 65 through 71 can have different volumes, such that the minimum possible liquid required for regeneration can be further reduced.

Turning now to FIG. 5, there is illustrated a block diagram of a first embodiment of a capacitive deionization-regeneration system 111 according to the present invention. The system 111 generally includes one or a stack of sequential (i.e., serially) electrochemical cells 30 (FIG. 3), an electrical circuit 112, and a fluid circuit 114, such that the fluid circuit 114 regulates the flow of the fluid stream through the cell 30, under the control of the electrical circuit 112.

Considering now the electrical circuit 112, it includes a voltage controlled D.C. power supply 117 which provides a constant D.C. voltage across the adjacent pairs of electrodes 35 through 43 (FIG. 3). A resistive load 120 and a switch 121 are connected in parallel, across the positive and negative terminals 122A, 122B, respectively, of the power supply 117, and are used to discharge, or regenerate the single electrochemical cell 30.

The electrical circuit 112 further includes a control system, as a triggering device to initiate regeneration. This control system utilizes on-line conductivity cells, ion selective electrodes, pH electrodes, polarographic sensors, impedance sensors, optical transmission cells, and light scattering sensors. The components that can be triggered by this on-line control system include power supplies, valves and pumps.

A differential amplifier 126 is connected across a shunt resistor 118, and is further connected to an analog-to-digital converter 127 and a computer 128. The shunt resistor 118 is used to measure the current flowing from the power supply 117 to the cell 30, for monitoring and control. The differential amplifier 126 amplifies the voltage across the shunt resistor 118 to a level that is monitorable by the analog-to-digital converter 127 and the computer 128. Another differential amplifier 125 is connected across the terminals 122A, 122B of the power supply 117, via the shunt resistor 118, and operates as a buffer between the power supply 117 and the analog-to-digital converter 127, for protecting the analog-to-digital converter 127.

The differential amplifier 125 is connected across the terminals of the cell 30, and serves as a buffer between the cell 30 and the A/D converter 127. In operation, as the cell 30 is used to deionize the electrolyte, the switch 121 is open. In order to start the regeneration process, the power supply 117 is turned off, or disconnected, and the switch 121 is closed, for providing a path for the discharge current.

The analog-to-digital converter 127 is connected to the inlet stream of the fluid circuit 114, via a plurality of sensors, such as a thermocouple 134, a conductivity probe 135, and a pH sensor 136, via respective transducers 131, 132 and 133. The thermocouple 134 enables the monitoring of the temperature of the inlet stream, in order to prevent the overheating of the electrolyte, and further enables the calibration of the conductivity probe 135. The conductivity probe 135 is an on line sensor which permit the monitoring of the conductivity of the inlet stream. The pH sensor measures the pH level of the inlet stream. The transducers 131, 132 and 133 convert the measurements of the thermocouple 134, conductivity probe 135 and pH sensor 136 into voltages that are readable by and compatible with the analog-to-digital converter 127. A flow rate meter 154 measures the flow rate of the inlet stream.

The fluid circuit 114 includes a feed and recycle tank 150 which contains the raw fluid to be processed by the cell 30. It should be understood that the fluid stored in the feed and recycle tank 150 can be replaced with a continuous inflow of raw fluid. A valve 151 is fluidly connected between the feed and recycle tank 150 and a pump 152. The speed of the pump 152 is used to control the flow rate of the inlet stream to the cell 30. The outlet stream is respectively connected, via two valves 156, 157, to a product tank 160 for storing the purified fluid, and to the feed and recycle tank 150. Valves 156 and 157 are used to select the mode of operation: batch mode or complete recycle; continuous mode or once through.

Similarly to the inlet stream, the analog-to-digital converter 127 is also connected to the outlet stream of the fluid circuit 114, via three transducers 141, 142, 143, a thermocouple 144, a conductivity probe 145, and a pH sensor 146.

In the continuous mode of operation, the raw fluid or electrolyte to be deionized is initially stored in the feed and recycle tank 150, and the valve 157 is closed. The pump 152 is activated for pumping the fluid from the feed and recycle tank 150 to the cell 30, where the fluid stream is deionized and purified, as described above. The purified effluent is then routed to the product tank 160 via the open valve 156. In certain applications, it would be desirable to recycle the fluid stream more than once, in order to obtain the desired level of purification. In which case, the valve 156 is closed, and the valve 157 is opened, in order to allow the fluid stream to be recycled through the cell 30.

When the cell 30 is saturated, the deionization process is automatically interrupted and the regeneration process starts. For this purpose, the power supply 117 is disconnected, and a regeneration tank (not shown) is fluidly connected to the pump 152 and the cell 30. The regeneration tank contains a suitable regeneration solution (only a relatively small amount of regeneration solution is needed and can have the same composition as the feed stream, for instance raw water), or alternatively, pure water can be used. The regeneration solution is passed through the cell 30, and the regeneration process takes place by placing the removed ions back into the regeneration solution.

In the event the electrodes become saturated with organic contaminants, it is possible to clean and regenerate the carbon composite electrode 44, or other porous monolithic electrodes by passing solutions of chemically and electrochemically regenerated oxidants, including but not limited to Ag(II), Co(III), Fe(III), ozone, hydrogen peroxide, and various bleaches, through the electrochemical cell 30.

Figure 12:
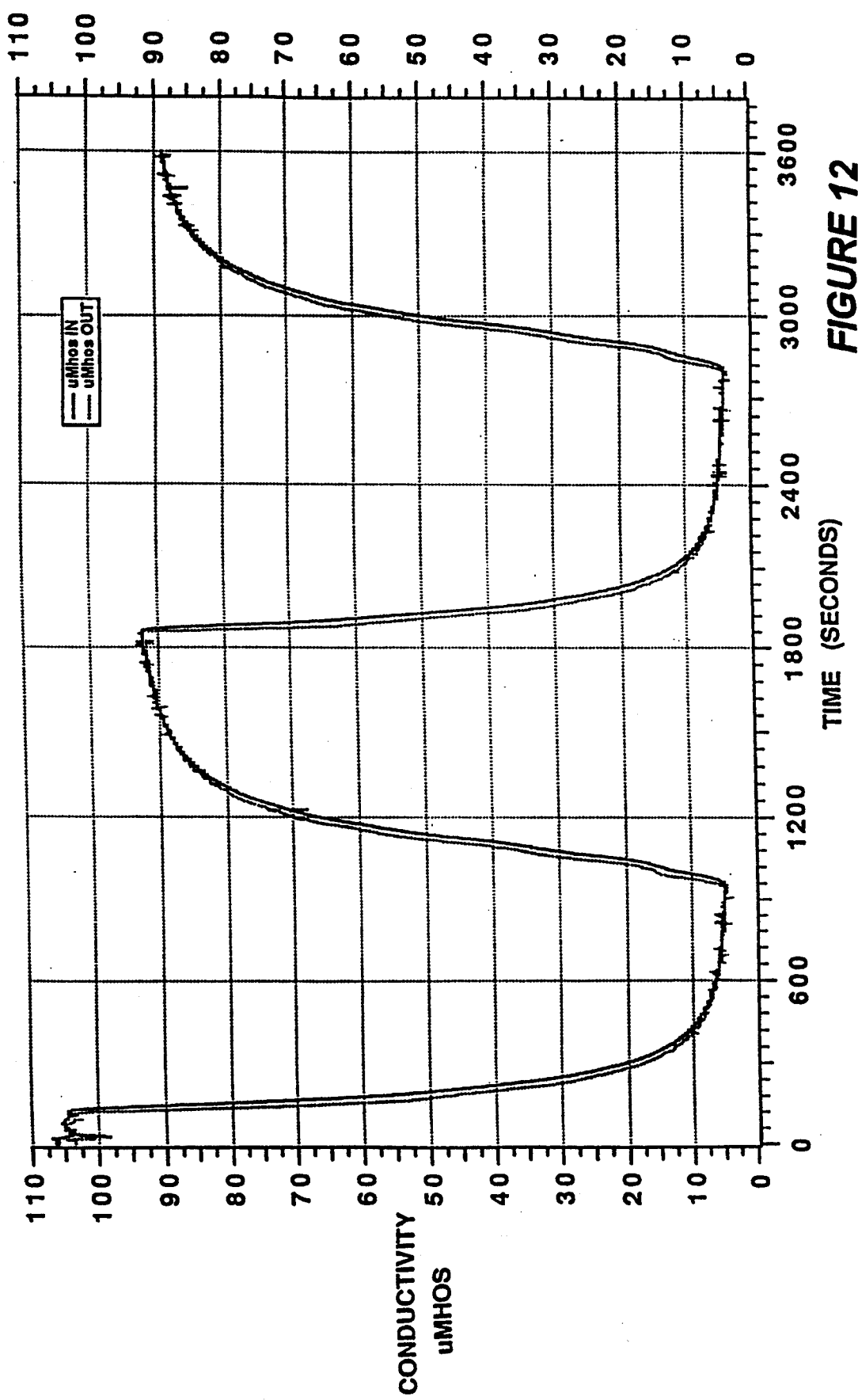
FIGS. 12 through 14 represent empirical timing charts using the capacitive deionization-regeneration system of FIG. 5.
Figure 13:
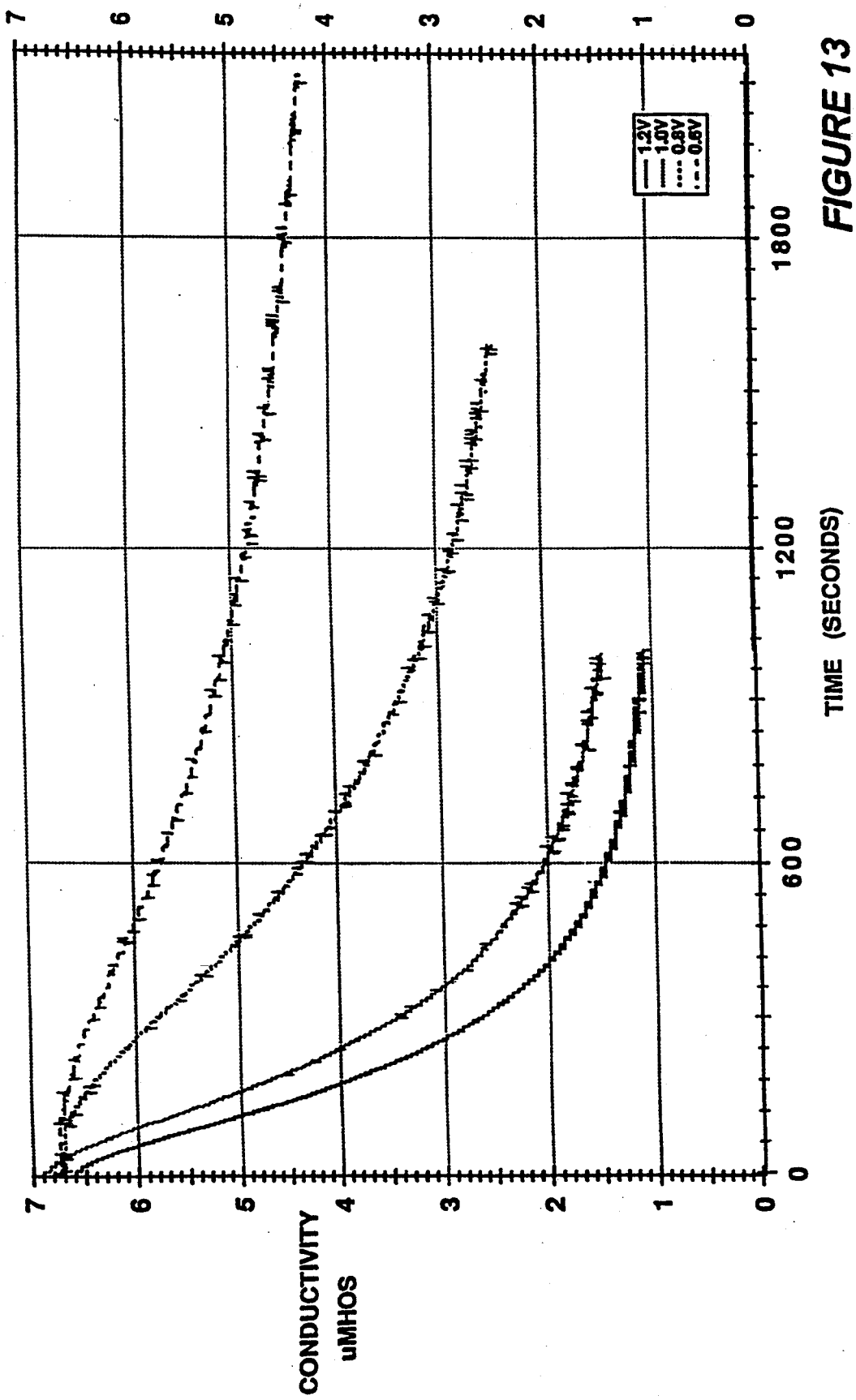
Figure 14:
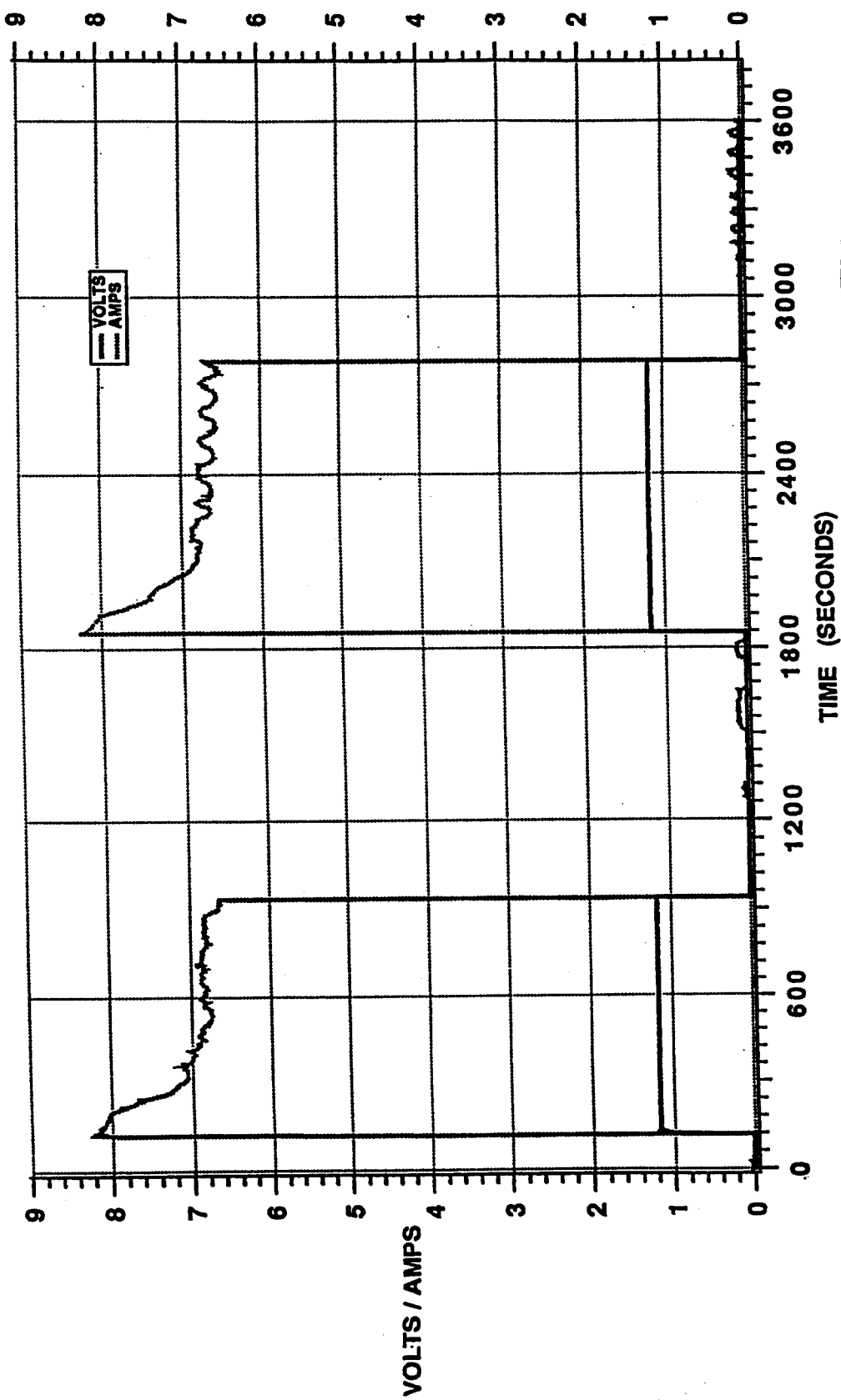

FIGS. 12 through 14 represent empirical timing charts using the capacitive deionization-regeneration system 111 of FIG. 5.

Figure 6:
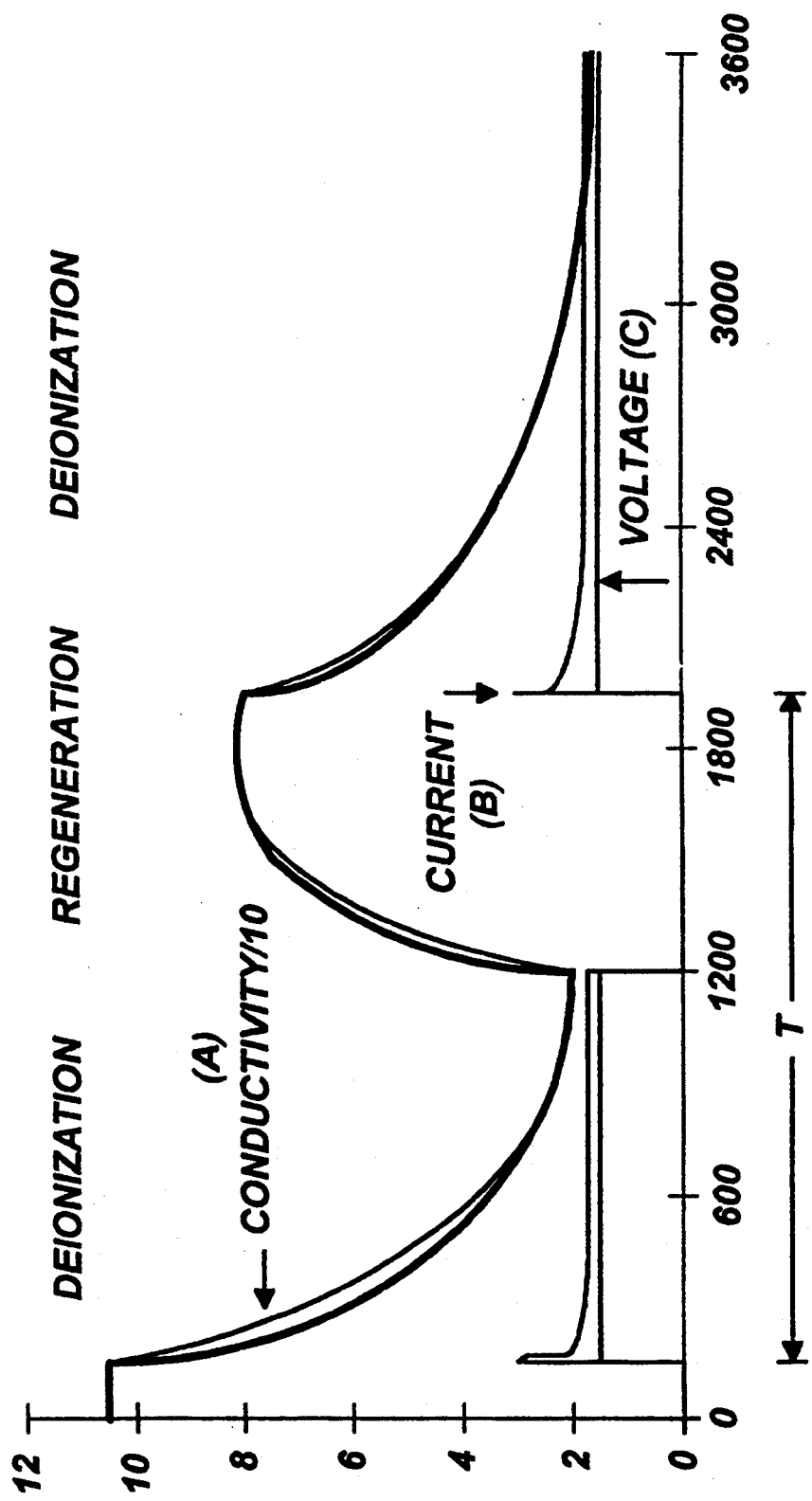
FIG. 6 includes three superposed timing charts illustrating the operation of the capacitive deionization-regeneration system of FIG. 5.

FIG. 6 includes three superposed timing charts A, B, C, illustrating the operation of the capacitive deionization-regeneration system 111 of FIG. 5, used for the deionization and regeneration of 100 micromho of NaCl solution. Chart A represents the conductivity of the electrolyte, and includes two curves, one illustrating the inlet stream conductivity and the other curve illustrating the outlet stream conductivty. Chart B represents the current flowing through the cell 30. Chart C represents the voltage across the cell 30. T represents the deionization-regeneration cycle.

Figure 8A:
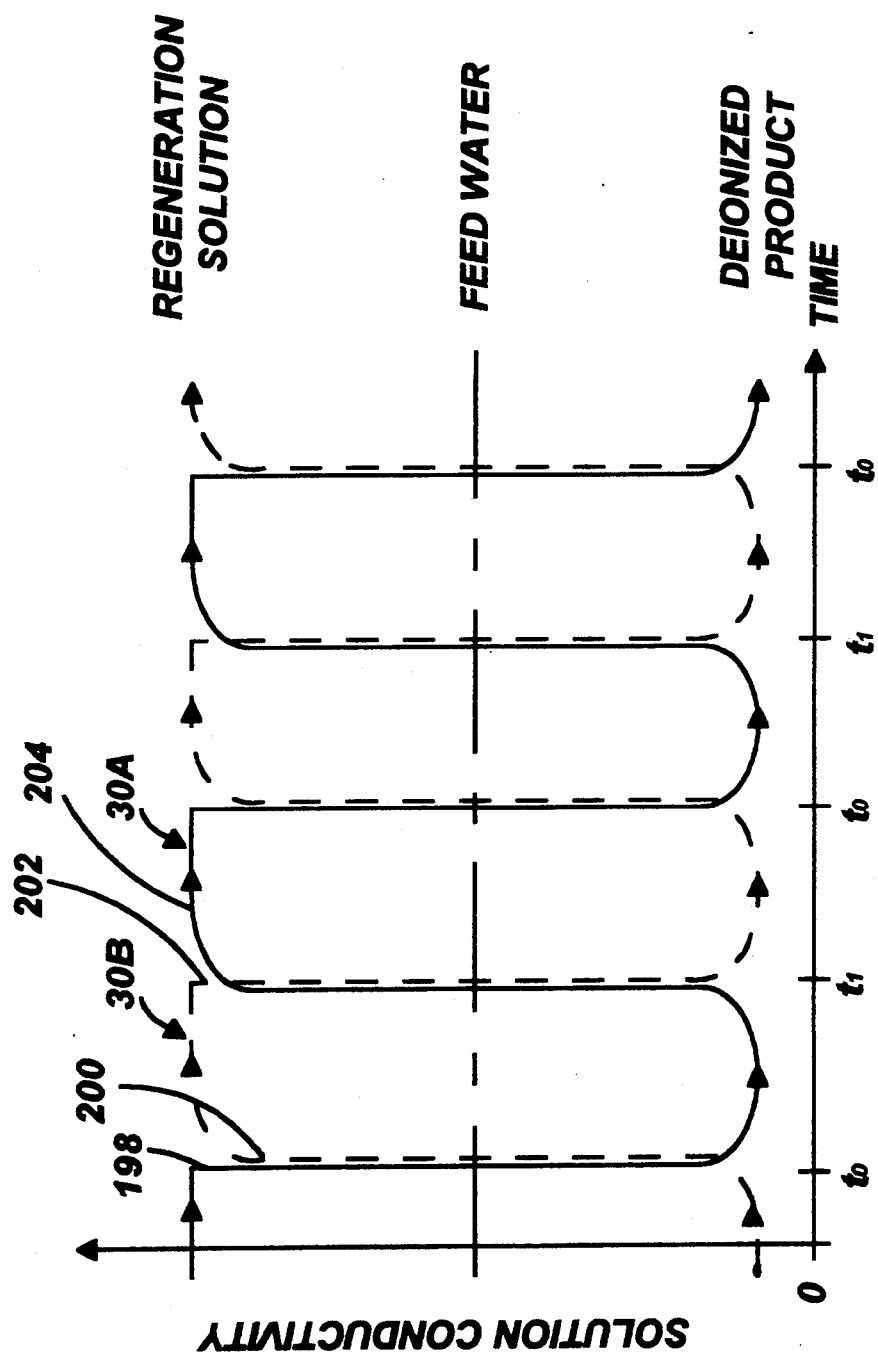
FIGS. 8(A-C) includes three timing charts A, B and C illustrating the operation of the, capacitive deionization-regeneration system of FIG. 7.
Figure 8C:
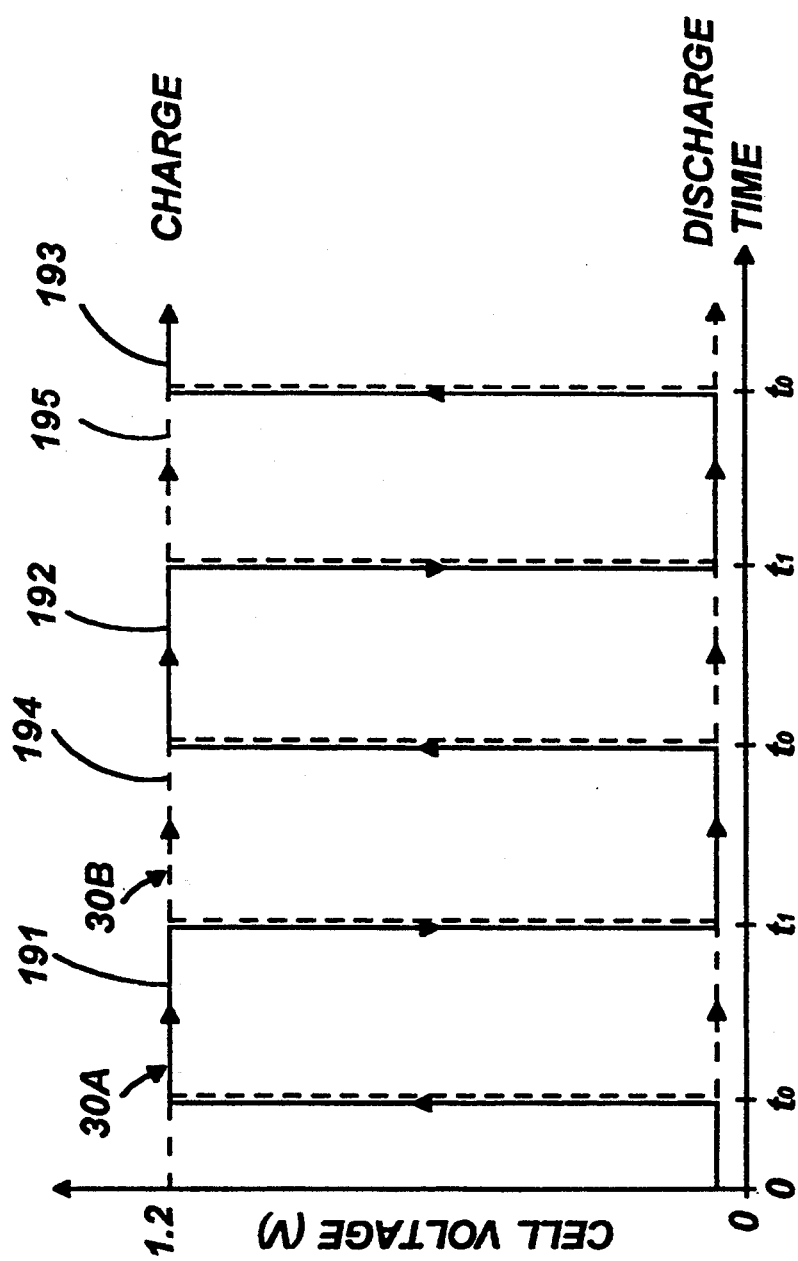

FIG. 7 illustrates a second embodiment of the capacitive deionization-regeneration system 175 using at least two parallel electrochemical cells 30A and 30B, both similar to the cell 30 shown in FIG. 3. FIG. 8 illustrates an exemplary operation of the capacitive deionization system 175 using 100 micromhos NaCl solution. One of the main advantages of the system 175 is its ability to maintain a continuous deionization and regeneration operation. The system 175 is generally similar to the system 111, and uses two cells 30A and 30B, such that when one cell 30A or 30B is deionizing the fluid stream while the other cell is regenerating, in preparation for the deionization process. Therefore, the operation of the system 175 is cyclical and continuous. For each one of the cells 30A and 30B, each cycle includes two half cycles. The first half cycle being the deionization process, and the second half cycle being the regeneration process, such that the cycles of the cells 30A and 30B are essentially 180 degrees out of phase.

The system 175 includes a power supply and switching apparatus 176 connected across both cells 30A and 30B, for selectively operating these cells. For instance, while the preferred embodiment of the system 175 includes operating one cell for deionizing a fluid stream, while the other cell is simultaneously being regenerated, it should be understood that both cells 30A and 30B can simultaneously perform the same process, i.e., deionization or regeneration.

A controller 178 regulates a plurality of inflow and outflow valves 179, 180a, 180b, 180c, 181a, 181b, 181c, and 182, for controlling the flow of the fluid stream to and from the cells 30A and 30B. An analog-to-digital converter 185 converts measurement signals from a plurality of conductivity and ion specific sensors 187, 188 disposed along the fluid circuit of the system 175, and transmits corresponding digital signals to a computer 190, which controls the controller 178, the power supply and switching apparatus 176, and thus the overall operation of the system 175. While only two sensors 187, 188 are shown merely for illustration purpose, other sensors can also be included to provide additional feedback data to the computer 190.

The operation of the system 175 will now be further described in relation to FIG. 8. FIG. 8 includes three timing charts A, B and C illustrating the operation of the capacitive deionization-regeneration system 175 of FIG. 7. In this particular case, no electrical power released during the regeneration of one cell is used by the other cell for deionization. Chart A shows the conductivity (micromhos) versus time (seconds), of the effluent fluid streams flowing from the cells 30A and 30B. Chart B shows the current (amperes) flowing through the cells 30A and 30B. Chart C shows the voltage (volts) applied across each cell 30A, 30B. In the case of aqueous (water-based) streams, optimum performance is obtained with a voltage pulse having an amplitude of 0.6–1.2 volts. Lower voltages diminish the capacity of the electrodes while significantly higher voltages cause electrolysis and associated gas evolution from the electrodes. Merely for clarity purpose, the solid lines in these charts A, B, C, relate to the behavior of the cell 30A, while the phantom or broken lines relate to the behavior of the cell 30B.

Considering now Chart C, the solid line illustrates a series of square shaped voltage pulses 191, 192, 193 applied across the cell 30A, with a plateau value of about 1.2 volts, while the broken line illustrates a series of square shape voltage pulses 194, 195 applied across the cell 30B, also with a plateau value of about 1.2 volts. It should however be understood that different voltages can be applied. Specifically, in the case of aqueous streams, the preferred voltages range between 0.6 and 1.2 volts. The voltage pulses applied to cells 30A and 30B are 180 degrees out of phase.

The voltage pulse 191 in Chad C will cause the cell 30A to progress with the deionization process, as illustrated by the current curve 197 in chart B, and by the conductivity curve 198 in chart A. While the voltage pulse 191 in Chad C is applied across the cell 30A, the anodes and cathodes of cell 30B are connected together through an external load, causing cell 30B to regenerate, as illustrated by the current curve 199 in chart B, and by the conductivity curve 200 in chart A.

Thereafter, the voltage pulse 194 is applied across the cell 30B causing it to progress with the deionization process, as illustrated by the current curve 201 in chart B, and by the conductivity curve 202 in chart A. While the pulse 194 is applied across the cell 30B, the anodes and cathodes of cell 30A are connected together through an external load, causing cell 30A to regenerate, as illustrated by the current curve 203 in chart B, and by the conductivity curve 204 in chart A.

The foregoing deionization-regeneration cycle enables the system 175 to operate continuously without interruption, since, as one of the cells 30A, 30B becomes saturated, the other cell is almost or completely regenerated, and is ready to proceed with the deionization process. As a result, the purified fluid stream at the output of the system 175 is continuous. The operation of the system 175 might be particularly attractive in nuclear power plants for scavenging contaminants from boiler water.

To briefly summarize the operation of the system 175, during the deionization process, the corresponding cell, either 30A or 30B, capacitively charges the electrode pairs forming it, thereby removing ions from the fluid stream passing through it. At the beginning of the deionization process, the cell has been completely and electrically discharged; at the end of the deionization process, the cell has been completely and electrically charged. Subsequently, during the regeneration process, the corresponding cell, either 30A or 30B, capacitively discharges the electrode pairs forming it, thereby placing ions into the fluid stream passing through it, greatly increasing the concentration of ions in that stream. At the beginning of the regeneration process, the cell has been completely and electrically charged; at the end of the regeneration process, the cell has been completely and electrically discharged.

Figure 9:
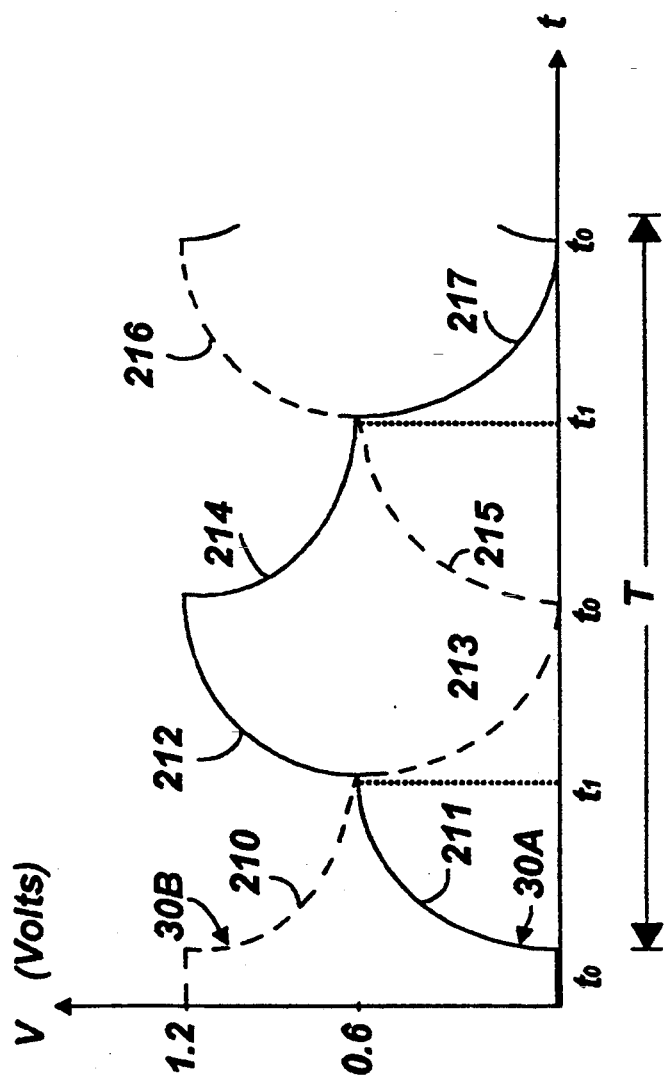
FIG. 9 is a timing chart illustrating the energy saving mode of the system shown in FIG. 7.

FIG. 9 illustrates another characteristic of the present invention, namely an enhanced energy efficiency or energy saving mode. In this particular mode of operation, a timing chart is used to illustrate the potential across each of the cells 30A and 30B, where the solid lines relate to the behavior of the cell 30A, while the broken lines relate to the behavior of the cell 30B. Starting at time $t_0$, the cell 30B is fully charged and ready to be regenerated, while the cell 30A is fully discharged and ready to begin the deionization process.

While it would be possible to disconnect the cell 30B from the power supply 176, and to connect the power supply 176 to the cell 30A, it is now possible to save energy, and in certain applications, save a significant fraction of the energy required to operate the system 175. According to the present invention, at time $t_0$, the cells 30A and 30B can be connected, such that cell 30B is discharged through the cell 30A, as indicated by the curve 210, causing the cell 30A to be charged, as indicated by the curve 211. Electrical energy stored in the cell 30B is used to power the cell 30A during deionization in the cell 30A.

As soon as an equilibrium voltage is reached, i.e., approximately 0.6 volts at time $t_1$, the cell 30A is connected to the power supply 176 so that the charging process can be completed, as illustrated by the curve 212. Simultaneously, the cell 30B is completely discharged through an external load, as indicated by the curve 213. As a result, a significant portion of the energy required to charge the cell 30A is generated by the cell 30B, with the remaining energy supplied by the power supply 176.

Thereafter, at time $t_2$, the cell 30A is fully charged and is ready for regeneration, while the cell 30B is completely discharged, and is ready for the deionization process. The cells 30A and 30B are then connected, such that the cell 30A is discharged through the cell 30B, as illustrated by the curve 214, while the cell 30B is charged, as illustrated by the curve 215.

As soon as the equilibrium voltage is reached at time $t_3$, the cell 30B is connected to the power supply 176 so that the charging process can be completed, as illustrated by the curve 216, and the cell 30A is allowed to completely discharge through an external load, as illustrated by the curve 217. As a result, a significant portion of the energy required to charge the cell 30B is generated by the cell 30A, with the remaining energy supplied by the power supply 176.

Figure 10:
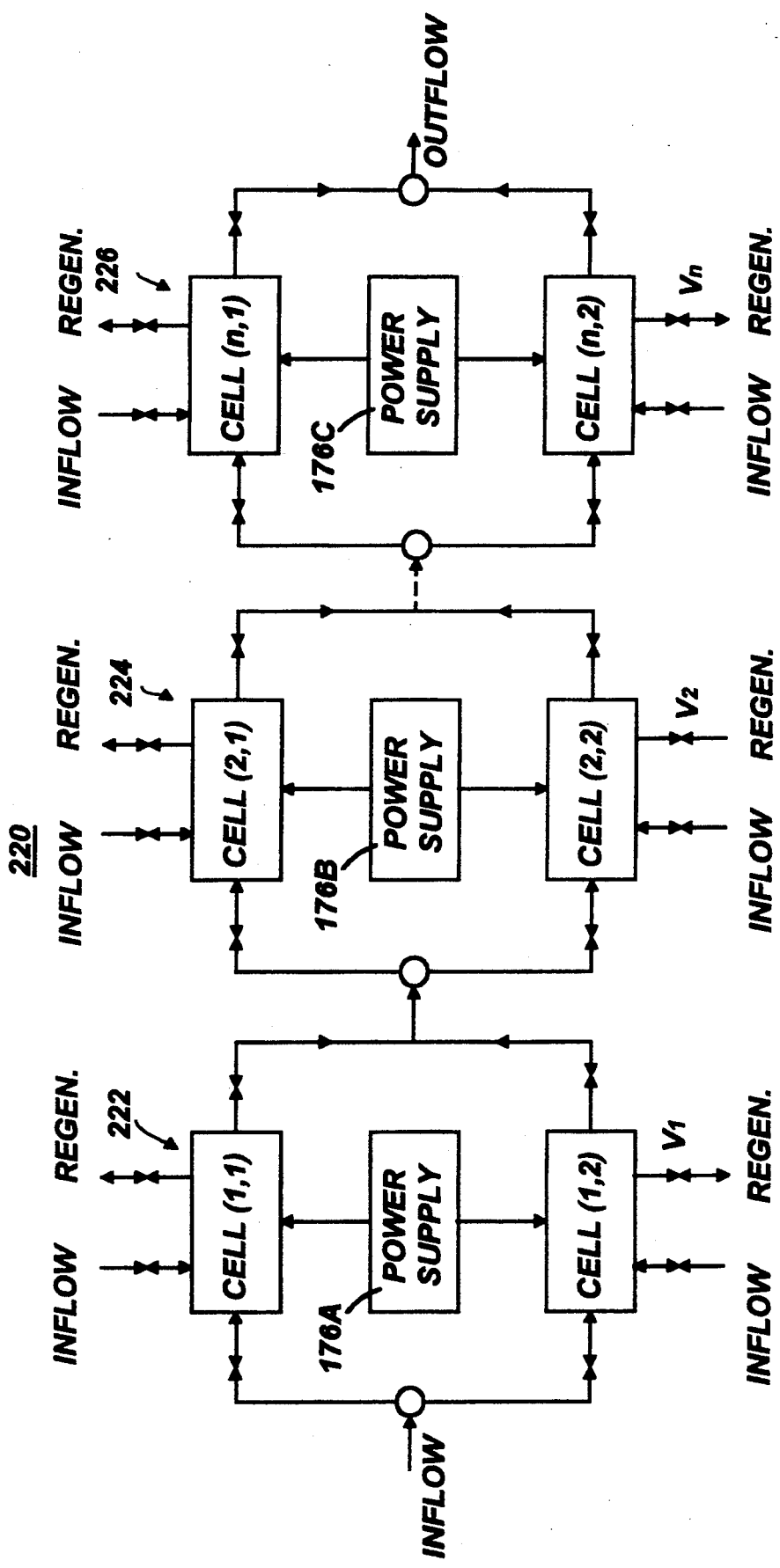
FIG. 10 is a block diagram representation of a third embodiment of a deionization-regeneration system according to the present invention.

Turning now to FIG. 10, it is a block diagram representation of a third embodiment of a deionization-regeneration system 220 according to the present invention. The system 220 includes a matrix of systems 222, 224, 226 similar to the system 175 (FIG. 7), which are connected in series. Each system includes at least one pair of cells which are connected and which operate as described in relation to the system 175. Thus, the system 222 includes cells (1,1) and (1,2); the system 224 includes cells (2,1) and (2,2); and the system 226 includes cells (n,1) and (n,2). Each of the systems 222, 224 and 226 includes a power supply and switching system 176A, 176B, 176C, respectively, which is similar to the power supply and switching system 176 shown in FIG. 7.

In operation, when one cell i.e., (1,1) of the pair of cell, i.e., 222 is performing the deionization process, the other cell, i.e., (1,2) is being regenerated. It should become clear to those skilled in the art that while only three systems 222, 224 and 226, each of which including two cells, are shown merely for illustration purpose, a different combination of systems or cells can be selected, without departing from the scope of the present invention.

One novel application for the system 220 is the progressive and selective deionization and regeneration feature. In other terms, different potentials ($V_1$, $V_2$, $V_n$) are applied across each system (222, 224, 226, respectively) in order to selectively deionize the influent fluid stream, by having each system (222, 224, 226) remove different ions from the fluid stream. Thus, in this particular example, $V_1 < V_2 < V_n$, such that the system 222 is capable of removing reducible cations such as $Cu^{++}$; the system 224 is capable of removing reducible cations such as $Pb^{++}$; and the system 226 is capable of removing non-reducible and non-oxidizable ions such as $Na^+$, $K^+$, $Cs^+$, $Cl^-$, or other similar ions, which remain in their ionic state.

By using the cells and systems according to the present invention, as described above, it is possible to remove the following impurities from aqueous streams and subsequently regenerate the cells:

1. Non oxidizable organic and inorganic anions. Inorganic anions include: $OH^-$, $Cl^-$, $I^-$, $F^-$, $NO_3^-$, $SO_4^{2-}$, $HCO_3^-$, $CO_3^{2-}$, $H_2PO_4^-$, $HPO_4^{2-}$, and $PO_4^{3-}$, etc. In this case, the operative mechanism is electrostatic double layer charging. For this purpose, it would be desirable to maintain the terminal potential across the electrodes lower than that required for electrolysis of the solvent in order to avoid gas evolution. The optimum potential is in the range between 1.0 and 1.2 volts, relative to the normal hydrogen electrode (NHE). In general, the recommended range of potential for water treatment lies between 0.6 and 1.2 volts.

2. Non reducible cations, such as $Li^+$, $Na^+$, $K^+$, $Cs^+$, $Mg^{++}$, $Ca^{++}$, etc. Here too the operative mechanism is electrostatic double layer charging.

3. Reducible cations, such as: $Cu^{++}$, $Fe^{++}$, $Pb^{++}$, $Zn^{++}$, $Cd^{++}$, etc. In this case, the operative mechanism is electrodeposition.

4. Colloidal particles such as bacteria, viruses, oxide particles, dirt, dust, etc. In this case, the operative mechanism is electrophoresis.

5. Chemisorption of organic molecules onto the carbon composite electrode 44. This adsorption process might be relatively irreversible. Regeneration in this case would involve the use of strong oxidants for the purposes of destroying the adsorbed organics (i.e., PCB).

One exemplary application of the present invention includes the design and manufacture of a deionization system for purifying radioactive water. For instance, one embodiment of the present system could be used to purify the waste water generated from washing fuel assemblies coated with metallic sodium residuals. The 500 gallons of waste water currently generated during the washing of each assembly include approximately 200 ppm sodium, trace quantities of other metals, trace quantities of some non-metal that can be removed by filtration, and trace quantities of radioactive constituents (primarily fuel cladding corrosion products). Grade B water purity would have to be achieved so that water could be recycled; (i.e., conductivity less than 20 microsiemens/cm).

Figures 11A, 11B:
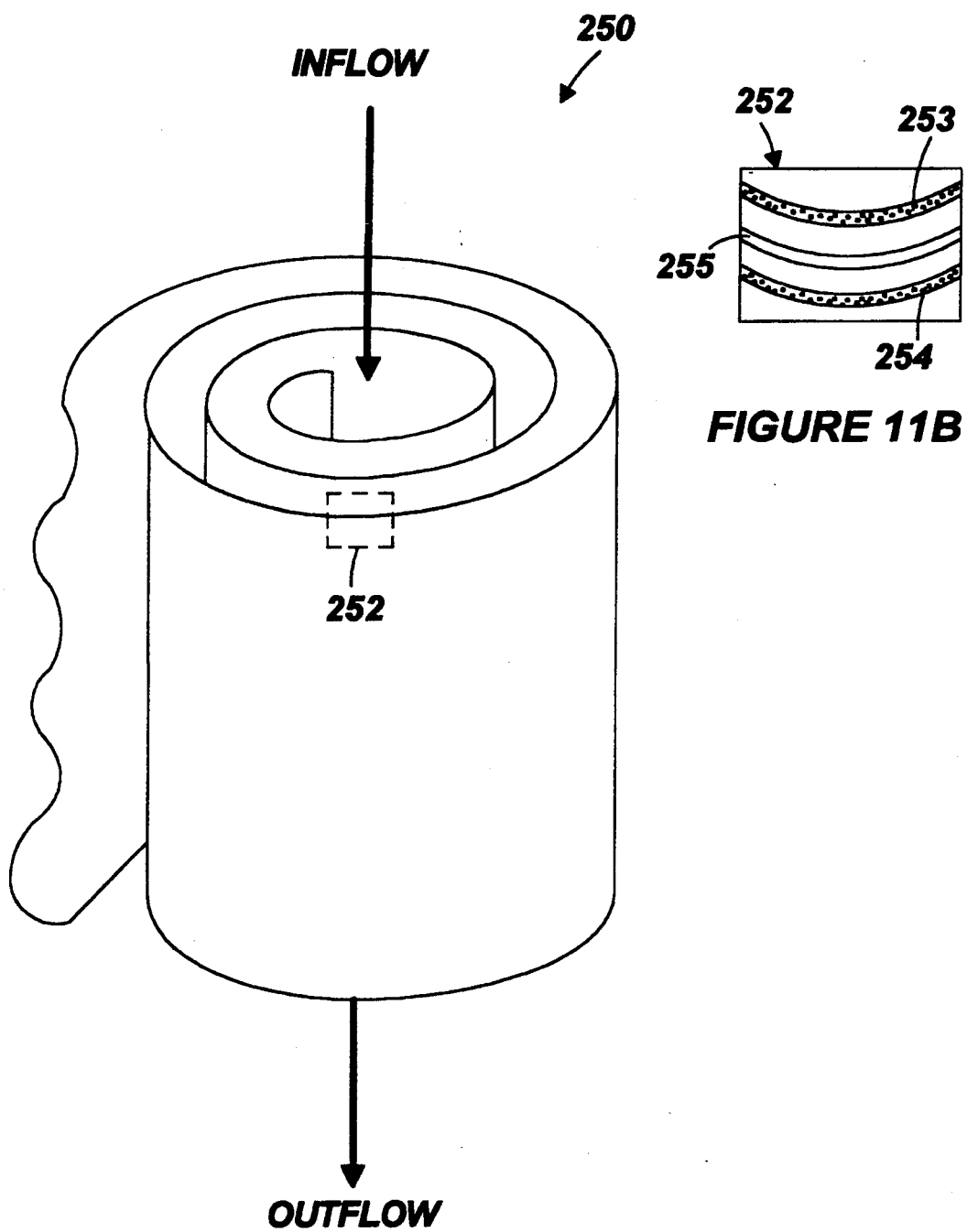
FIG. 11 is schematic isometric view of another embodiment of an electrochemical cell according to the present invention, which is also adapted for use as part of the capacitive deionization-regeneration systems of FIGS. 5 and 7.

Referring now to FIG. 11, it is a schematic isometric view of an electrochemical cell 250, with a portion 252 thereof enlarged. The cell 250 can be adapted for use as part of the capacitive deionization-regeneration systems 111 and 175 of FIGS. 5 an 7, respectively. The cell 250 includes a plurality of electrodes 253, 254 that are separated by a porous separator or membrane 255. The separator 255 is sandwiched between two adjacent electrodes 253, 254, and allows an open channel to be formed and defined therebetween. The electrodes 253 and 254 are similar to the electrodes of cells 30, 30A and 30B described above. The electrodes 253, 254 and the separator 255 are rolled spirally together, so that the electrolyte flows in the open channels formed between the electrodes 253, 254, and exits the cell 250 with minimal flow resistance. While the cell 250 has been described as including two electrodes 253, 254 and one separator 255 for illustration purpose, it should be understood that additional electrodes and separators can alternatively be used.

The foregoing description of the embodiments of the present invention has been presented for purposes of illustration and description. It is not intended to be exhaustive or to limit the invention to the precise forms described, and obviously many other modifications are possible in light of the above teaching. The embodiments were chosen in order to explain most clearly the principles of the invention and its practical applications, thereby to enable others in the art to utilize most effectively the invention in various other embodiments and with various other modifications as may be suited to the particular use contemplated.

What is claimed is:

1. An electrochemical cell comprising in combination:
   two oppositely disposed, spaced-apart end plates, one at each end of the cell;
   two generally identical single-sided end electrodes, one at each end of the cell, adjacent to said end plates;
   an insulator layer interposed between one of said end plates and an adjacent one of said end electrodes;
   an insulator layer interposed between the other end plate and the other one of said end electrodes;
   each single-sided electrode including a single sheet of conductive material having a high specific surface area and sorption capacity; and
   a plurality of generally identical double-sided intermediate electrodes being spaced-apart and equidistally separated from each other, between said two end electrodes.

2. The electrochemical cell according to claim 1, wherein said conductive material includes carbon aerogel composite.

3. The electrochemical cell according to claim 2, wherein each end electrode includes a sheet of carbon aerogel composite bonded to one side of a metallic structural support; and
   wherein each intermediate electrode includes two sheets of carbon aerogel composite bonded to both sides of a metallic structural support.

4. The electrochemical cell according to claim 3, wherein the number of said plurality of intermediate electrodes is at least 192.

5. The electrochemical cell according to claim 3, wherein said metallic structural support includes a titanium sheet.

6. The electrochemical cell according to claim 3, wherein each metallic structural support includes a plurality of apertures for providing passage to an electrolyte, through said end electrodes and said intermediate electrodes.

7. The electrochemical cell according to claim 6, wherein said specific surface areas of carbon aerogel composite electrodes range between 400 and 1000 $m^2/gm$.

8. The electrochemical cell according to claim 6, wherein said end electrodes and said intermediate electrodes are separated by a plurality of thin insulating gaskets with central apertures.

9. The electrochemical cell according to claim 6, wherein each pair of adjacent electrodes forms an open chamber adapted to fluidly communicate with a subsequent chamber via said plurality of apertures in said structural supports.

10. The electrochemical cell according to claim 9, wherein said apertures are not coaligned, and are positioned so that the electrolyte therethrough is forced to flow across all the exposed surfaces of said sheets of carbon aerogel composite.

11. The electrochemical cell according to claim 10, wherein the electrolyte path within said chambers is serpentine.

12. The electrochemical cell according to claim 11, wherein said end electrodes and said intermediate electrodes form a plurality of anodes and cathodes;
   wherein said anodes and cathodes are interleaved in an alternating way, such that every other electrode is an anode; and
   wherein each pair of adjacent anode and cathode forms a separate capacitive deionization/regeneration unit.

13. The electrochemical cell according to claim 12, wherein the each chamber formed within each deionization/regeneration unit allows the electrolyte to flow through said unit along a path parallel to the surfaces of said electrodes forming said unit.

14. The electrochemical cell according to claim 13, wherein when said deionization/regeneration units progressively and electrostatically remove ions from the electrolyte during a deionization process; and
   wherein said deionization/regeneration units progressively place the removed ions back into the electrolyte during the regeneration process.

15. The electrochemical cell according to claim 14, wherein the electrolyte flows through said deionization/regeneration units under the force of gravity.

16. The electrochemical cell according to claim 14, wherein the electrolyte is sea water; and
   wherein the deionization process includes desalting the electrolyte.

17. The electrochemical cell according to claim 14, wherein each chamber has a volume which corresponds to the minimum possible liquid volume required for regeneration.

18. The electrochemical cell according to claim 1, wherein said conductive material includes carbon aerogel particles.

19. A capacitive deionization-regeneration system comprising in combination:
   at least one electrochemical cell including:
   a. two oppositely disposed, spaced-apart end plates, one at each end of the cell;
   b. two generally identical single-sided end electrodes, one at each end of the cell, adjacent to said end plates;
   c. an insulator layer interposed between one of said end plates and an adjacent one of said end electrodes;
   d. an insulator layer interposed between the other end plate and the other one of said end electrodes;
   e. each single-sided electrode including a single sheet of conductive material having a high specific surface area and sorption capacity; and
   f. a plurality of generally identical double-sided intermediate electrodes being spaced-apart and equidistally separated from each other, between said two end electrodes; an electrical circuit for controlling the operation of the cell;
   a fluid circuit for regulating the flow of and electrolyte through the cell, under the control of the electrical circuit.

20. The deionization/regeneration system according to claim 18 further including at least two parallel electrochemical cells in order to maintain a continuous deionization and regeneration operation.

21. An electrostatic method for deionizing an electrolyte comprising the step of passing the electrolyte through an electrochemical cell including:
   a. two oppositely disposed, spaced-apart end plates, one at each end of the cell;

b. two generally identical single-sided end electrodes, one at each end of the cell, adjacent to said end plates;

c. an insulator layer interposed between one of said end plates and an adjacent one of said end electrodes;

d. an insulator layer interposed between the other end plate and the other one of said end electrodes;

e. each single-sided electrode including a single sheet of conductive material having a high specific surface area and sorption capacity; and f. a plurality of generally identical double-sided intermediate electrodes being spaced-apart and equidistally separated from each other, between said two end electrodes.

22. The method according to claim 21, further including the step of automatically interrupting the deionization process when the cell is saturated.

23. The method according to claim 22, further including the step of automatically starting a regenerating process of the cell when the deionization process is interrupted.

24. The method according to claim 22, further including the steps of:

using at least two parallel electrochemical cells in order to maintain a continuous deionization and regeneration operation; and operating a first one of said at least two cells for deionizing the electrolyte, while the other cell is simultaneously being regenerated.

25. The method according to claim 24, further including the steps of:

operating said at least two cells in an enhanced energy saving mode, whereby when either of said cells is fully charged and ready to be regenerated, the other cell is fully discharged and ready to begin the deionization process; and electrically connecting said cells, at least until an equilibrium voltage is reached.

26. The method according to claim 21, wherein said step of passing the electrolyte includes the step of removing various ions from waste water.

27. The method according to claim 21, wherein said step of passing the electrolyte includes the step of treating boiler water in nuclear and fossil power plants.

28. The method according to claim 21, wherein said step of passing the electrolyte includes the step of producing high-purity water for semiconductor processing.

29. The method according to claim 21, wherein said step of passing the electrolyte includes the step of softening home drinking water.

30. The method according to claim 21, wherein said step of passing the electrolyte includes the step of removing salt from water for agricultural irrigation.

31. The method according to claim 21, wherein said step of passing the electrolyte includes the steps of:

removing impurities from an aqueous stream; and subsequently regenerating said cell.

32. The method according to claim 31, wherein the removed impurities include non oxidizable organic and inorganic anions.

33. The method according to claim 31, wherein the removed impurities include non reducible cations.

34. The method according to claim 31, wherein the removed impurities include reducible cations.

35. The method according to claim 31, wherein the removed impurities include colloidal particles.

36. The method according to claim 31, wherein the step of removing impurities includes chemisorption of organic molecules.

37. An electrochemical cell comprising in combination:

a plurality of electrodes separated by a plurality of porous separators interposed between two adjacent electrodes;

each one of said plurality of electrodes including a single sheet of conductive material having a high specific surface area and sorption capacity;

each of said plurality of separators defining an open channel between two adjacent electrodes; and said plurality of electrodes separators being rolled spirally together, for allowing an electrolyte to flow in said open channel and to exit the cell with minimal flow resistance.

* * * * *